United States Patent
Uehata et al.

(10) Patent No.: US 8,187,295 B2
(45) Date of Patent: *May 29, 2012

(54) PUNCTURE DEVICE

(75) Inventors: Yoshiharu Uehata, Kyoto (JP); Masahiro Fukuzawa, Kyoto (JP)

(73) Assignee: Arkray, Inc. (JP)

( * ) Notice: Subject to any disclaimer, the term of this patent is extended or adjusted under 35 U.S.C. 154(b) by 43 days.

This patent is subject to a terminal disclaimer.

(21) Appl. No.: 10/553,523

(22) PCT Filed: Apr. 14, 2004

(86) PCT No.: PCT/JP2004/005338
§ 371 (c)(1),
(2), (4) Date: Oct. 14, 2005

(87) PCT Pub. No.: WO2004/091402
PCT Pub. Date: Oct. 28, 2004

(65) Prior Publication Data
US 2006/0206135 A1    Sep. 14, 2006

(30) Foreign Application Priority Data

Apr. 16, 2003 (JP) .................... 2003-111951
Sep. 22, 2003 (JP) .................... 2003-329547

(51) Int. Cl.
*A61B 17/32* (2006.01)

(52) U.S. Cl. ...................................... 606/182

(58) Field of Classification Search .............. 606/181, 606/182, 183, 184, 185; 600/583, 573, 578, 600/584; 604/136
See application file for complete search history.

(56) References Cited

U.S. PATENT DOCUMENTS

| | | | |
|---|---|---|---|
| 4,442,836 A | | 4/1984 | Meinecke et al. |
| 5,041,088 A | * | 8/1991 | Ritson et al. .................. 604/88 |
| 5,318,584 A | | 6/1994 | Lange et al. |
| 6,039,485 A | * | 3/2000 | Kageyama et al. .............. 401/67 |
| 6,152,942 A | | 11/2000 | Brenneman et al. |
| 6,156,050 A | * | 12/2000 | Davis et al. ................... 606/181 |
| 6,226,873 B1 | * | 5/2001 | Okumura ........................ 30/162 |
| 6,602,268 B2 | | 8/2003 | Kuhr et al. |
| 6,629,985 B1 | * | 10/2003 | Kiehne ........................ 606/167 |
| 7,244,266 B2 | * | 7/2007 | Garthe et al. ................. 606/181 |

(Continued)

FOREIGN PATENT DOCUMENTS

| | | |
|---|---|---|
| EP | 1 166 719 | 1/2002 |
| JP | 2702374 | 10/1997 |
| JP | 2001-425 | 1/2001 |
| WO | WO 02/36010 | 5/2002 |

*Primary Examiner* — Ryan Severson
*Assistant Examiner* — David Eastwood
(74) *Attorney, Agent, or Firm* — Studebaker & Brackett PC; Donald R. Studebaker

(57) ABSTRACT

The invention provides a lancing apparatus for moving a lancet holder (32) retaining a lancet in a lancing direction (N1) from a standby position to a lancing position together with the lancet so as to cause the lancet to stick into an object. In the lancing apparatus the lancet is inserted into the lancet holder (32) in a retreating direction (N2), thus to be retained by the lancet holder. The lancet holder (32) includes a first member and a second member (33, 34) relatively movable with respect to each other, so that the first and the second members (33), (34) are relatively moved so as to fix the lancet. Preferably, the lancet holder (32) is constructed such that at least either of the first and the second members (33, 34) applies a pressing force to the lancet, so as to fix the lancet.

21 Claims, 26 Drawing Sheets

U.S. PATENT DOCUMENTS

2002/0040230 A1* 4/2002 Kuhr et al. .................... 606/181
2002/0087180 A1* 7/2002 Searle et al. .................. 606/181
2003/0225429 A1* 12/2003 Garthe et al. ................. 606/182
2004/0034318 A1 2/2004 Fritz et al.

* cited by examiner

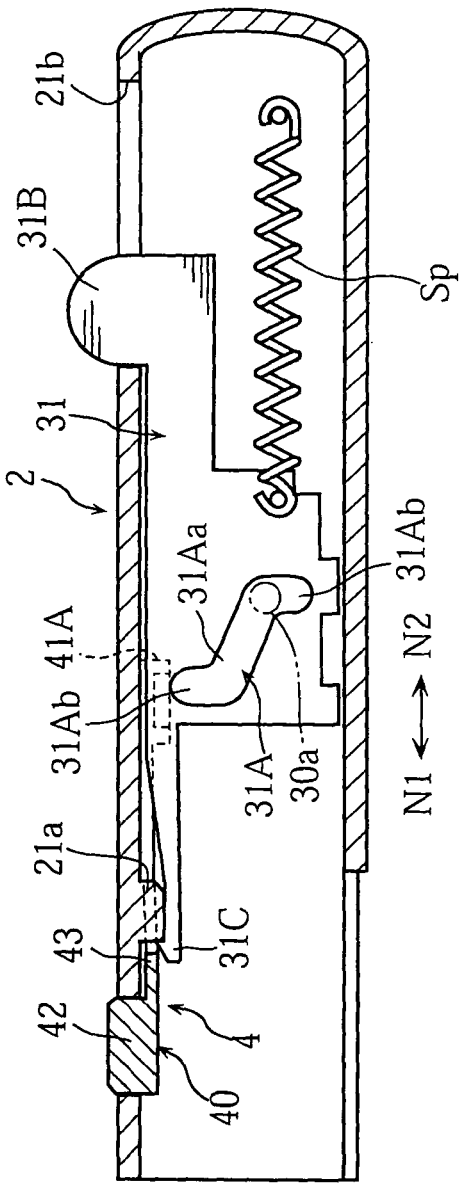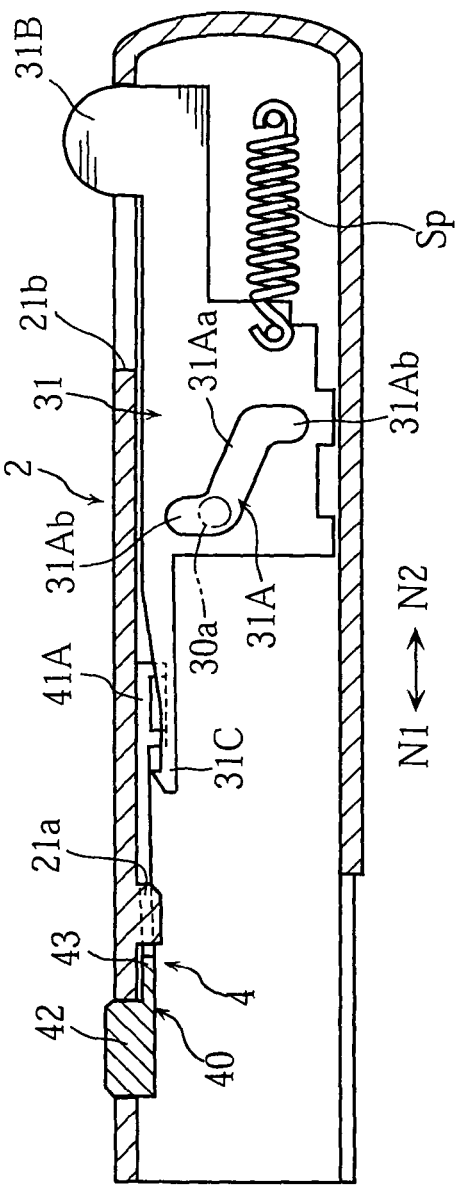

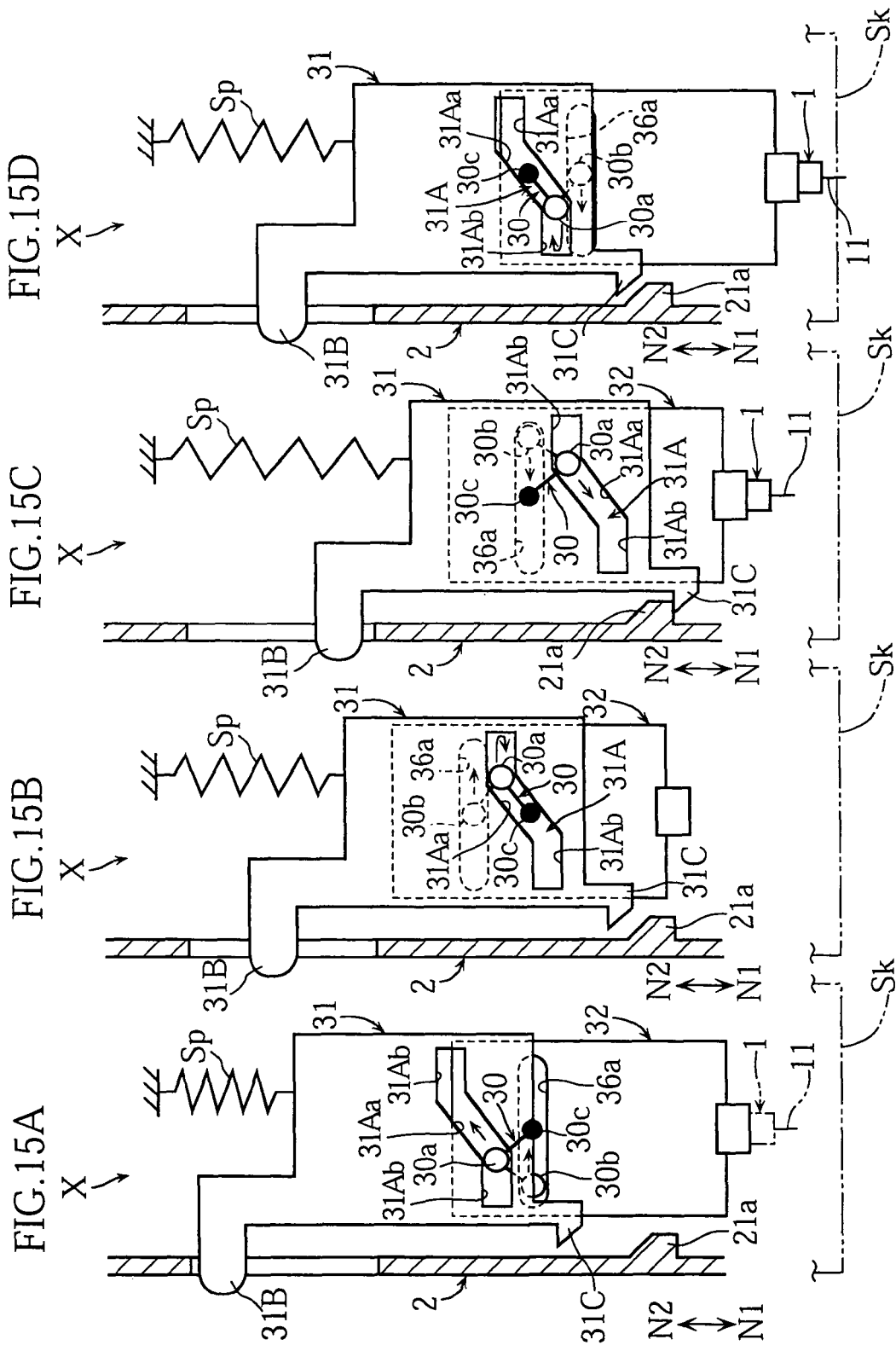

N1 ⟷ N2

N1 ⟷ N2

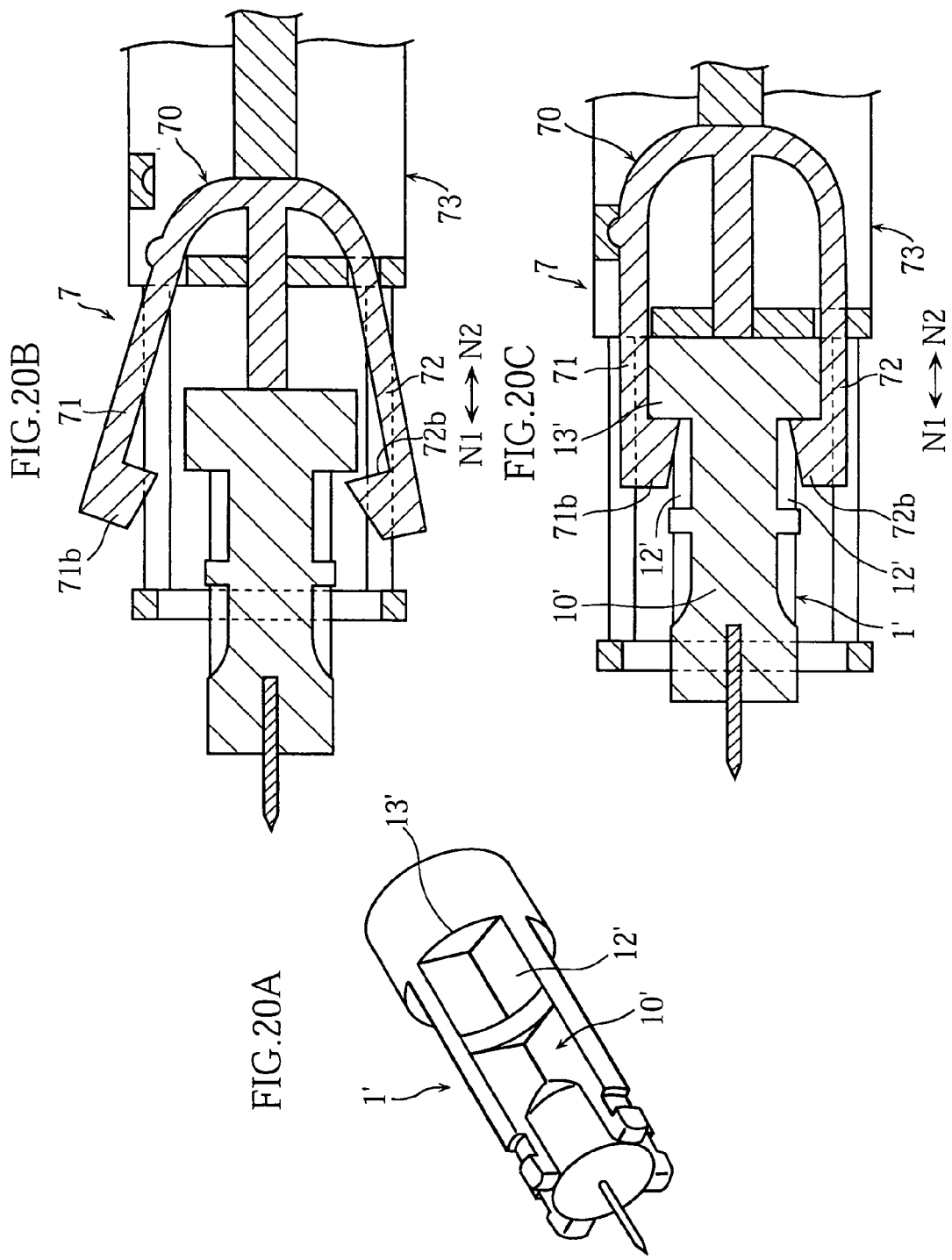

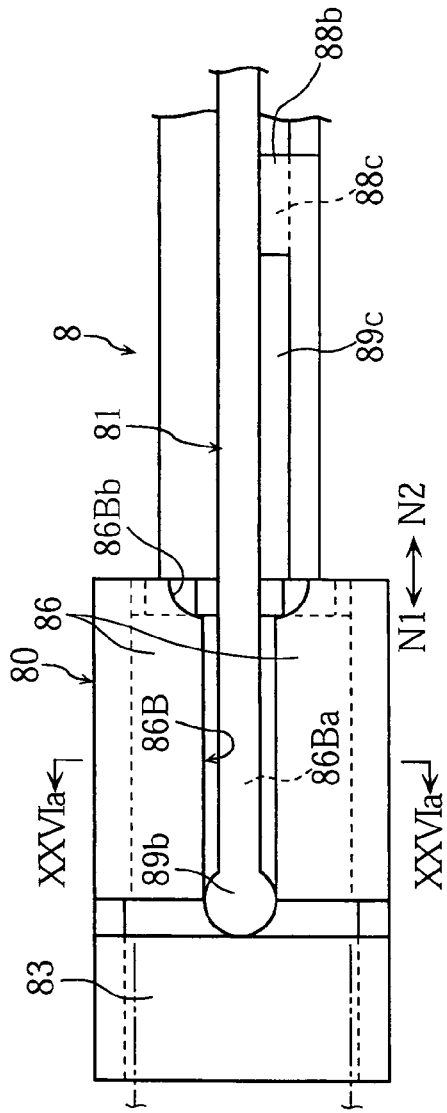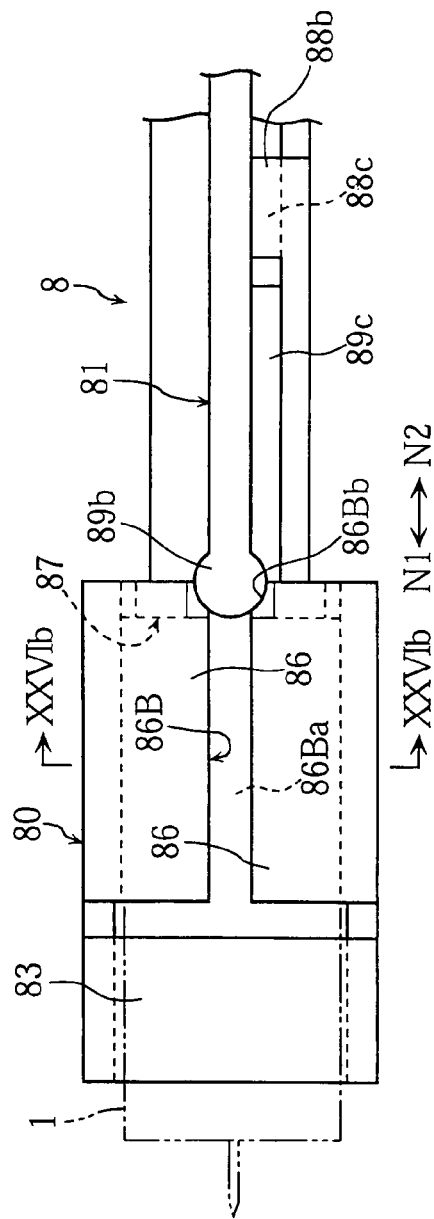

PUNCTURE DEVICE

TECHNICAL FIELD

The present invention relates to a lancing apparatus used for collecting e.g. blood or a tissue via skin.

BACKGROUND ART

Some of the existing lancing apparatuses include a lancet holder that holds a lancet, which is caused to move together with the lancet holder so as to stick into a skin (see JP-A-2001-425 for example). The lancing motion of the lancing apparatus disclosed in this document can be achieved by the structure of a lancing apparatus 9 shown in FIGS. 32A-32C. The lancing apparatus 9 utilizes the spring force of a coil spring 90, thereby moving a lancet 92 together with a lancet holder 91.

In the lancing apparatus 9, as shown in FIG. 32A, an engaging hook 93 of the lancet holder 91 is latched on a stepped portion 95 of the housing 94, so that the coil spring 90 can store the spring force. When an operating knob 96 is pressed down, a working portion 97 of the operating knob 96 acts on the engaging hook 93 as shown in FIG. 32B, so as to release the engaging hook 93. This permits the spring force of the coil spring 90 to act on the lancet holder 91 as shown in FIG. 32C, so that the lancet 92 is moved in a lancing direction N1 together with the lancet holder 91.

As is apparent from FIG. 32C, in the lancing apparatus 9 the lancet 92 is inserted into a bore 98 of the lancet holder 91, to be retained. The lancet 92 is retained by friction between the outer surface of the lancet 92 and the inner surface of the bore 98. With such an arrangement, a relatively large frictional resistance is required between the outer surface of the lancet 92 and the inner surface of the bore 98, in order to enable the lancet holder 91 to firmly retain the lancet 92. Conventionally, it is difficult to check whether the lancet 92 has been fully inserted into the bore 98 of the lancet holder 91, when loading the lancet 92 in the bore 98. The structure of the lancing apparatus 9 allows the lancing action to be performed regardless of whether the lancet 92 is fully inserted into the bore 98. Thus, it could happen that the lancing action may be performed, with the lancet 92 inserted only halfway into the bore 98. In this case, the lancet 92 may stick too deeply into the skin. Further, the large frictional resistance between the outer surface of the lancet 92 and the inner surface of the bore 98 incurs additional drawbacks. For example, it requires a relatively large force for inserting the lancet 92 into the bore 98, and also makes it difficult to remove the lancet 92 from the lancet holder 91.

It could be an option to redesign both of the lancet and the lancet holder so as to allow the lancet to be securely loaded in position on the lancet holder and to be easily removed from the holder, in order to eliminate the foregoing drawbacks. Redesigning the shape of the lancet, however, reduces the compatibility of the lancet with different types of lancing apparatuses, thus spoiling the versatility of the lancet.

DISCLOSURE OF THE INVENTION

Accordingly, it is an object of the present invention to provide a lancing apparatus with which an existing lancet is properly loaded into the lancet holder without modifying the design of the lancet, and also with which the loaded lancet is easily removed.

The present invention provides a lancing apparatus comprising a lancet holder for retaining a lancet. The lancet holder is movable in a lancing direction from a standby position to a lancing position together with the lancet so as to cause the lancet to stick into an object. The lancet is inserted into the lancet holder in a retreating direction which is opposite to the lancing direction, and retained by the lancet holder. The lancet holder includes a first member and a second member that are movable relative to each other. The first and the second members are relatively moved so as to fix the lancet to the holder.

Preferably, in the lancing apparatus, at least one of the first and the second members applies a pressing force to the lancet for fixing the lancet.

In the lancing apparatus according to the present invention, when loading the lancet for example, the first member relatively moves with respect to the lancet, while the second member moves together with the lancet with respect to the first member in the retreating direction from a first position toward a second position. In this case, it is preferable that the lancet holder applies a greater pressing force to the lancet when the second member is located at the second position, than when the second member is at the first position.

In the lancing apparatus according to the present invention, it is preferable that the second member includes fixing means that applies a pressing force to the lancet so as to fix the lancet when the second member is at the second position. In this case, it is preferable that the first and the second members respectively include a first engaging portion and a second engaging portion that are engaged with each other when the second member is at the second position, and that constitute the fixing means. At least one of the first and the second engaging portions is formed so as to project toward the other of the first and the second engaging portions. Preferably, one of the first and the second engaging portions comprises a recess, while the other of the first and the second engaging portions comprises a projection to be fitted into the recess.

The first member may include a pressing portion that applies a pressing force to the lancet. In this case, it is preferable that the second member includes a working portion that displaces at least a part of the pressing portion so as to separate from the lancet when the second member is at the first position or between the first position and the second position.

The pressing portion may include a pair of movable portions, between which is defined a gap through which the working portion is caused to move. The gap is expanded when the working portion moves through the gap, so that at least a part of the movable portions is displaced so as to separate from the lancet. At least one of the movable portions may include at least one cutaway that defines a part of the gap, and that the working portion is fitted into.

The above-mentioned cutaway may comprise a first cutaway portion into which the working portion is fitted in fixing the lancet, and a second cutaway portion into which the working portion is fitted in discharging the lancet. The cutaway portion may be arranged to make the gap continuously or incrementally narrower when the working portion relatively moves with respect to the first member in the lancing direction. Specifically, the cutaway portion preferably includes at least one tapered portion that makes the gap wider continuously as proceeding in the lancing direction, and may also include at least one stepped portion that makes the gap wider sequentially as proceeding in the lancing direction.

The pressing portion may include a fixed portion and a movable portion that define a gap through which the working portion is moved. In this case, the gap is expanded when the working portion moves through the gap, so that at least a part of the movable portions is displaced so as to separate from the lancet.

The second member may include a pair of movable portions for holding the lancet therebetween. In this case, the movable portions are displaced so as to separate from the lancet when the second member is relatively moved with respect to the first member in the lancing direction, while also being displaced toward the lancet when the second member is relatively moved with respect to the first member in the retreating direction.

Use may be made of a lancet provided with a recessed portion. In this case, the movable portion may include an engaging portion to be engaged with the recessed portion of the lancet.

Preferably, the lancing apparatus according to the present invention may further comprise a pushing member that moves the second member in the lancing direction. The pushing member may include a working portion to interfere with the second member and an operating portion to be manipulated so as to move the working portion.

BRIEF DESCRIPTION OF THE DRAWINGS

FIGS. 6A and 6B are simplified cross-sectional views showing the internal structure of the lancing apparatus shown in FIG. 1;

FIGS. 15A to 15D are schematic drawings for explaining a lancing action performed by the lancing apparatus shown in FIG. 1;

FIGS. 20A to 20C are drawings for explaining a lancet holder according to a third embodiment of the present invention, among which FIG. 20A is a perspective view showing the lancet, and FIGS. 20B and 20C are fragmentary cross-sectional views showing how the lancet is loaded on the lancet holder;

FIGS. 25A and 25B are fragmentary plan views showing the lancet holder shown in FIG. 21;

BEST MODE FOR CARRYING OUT THE INVENTION

Referring to the accompanying drawings, a first to a fifth embodiments of the present invention will be described below.

Figure 1:
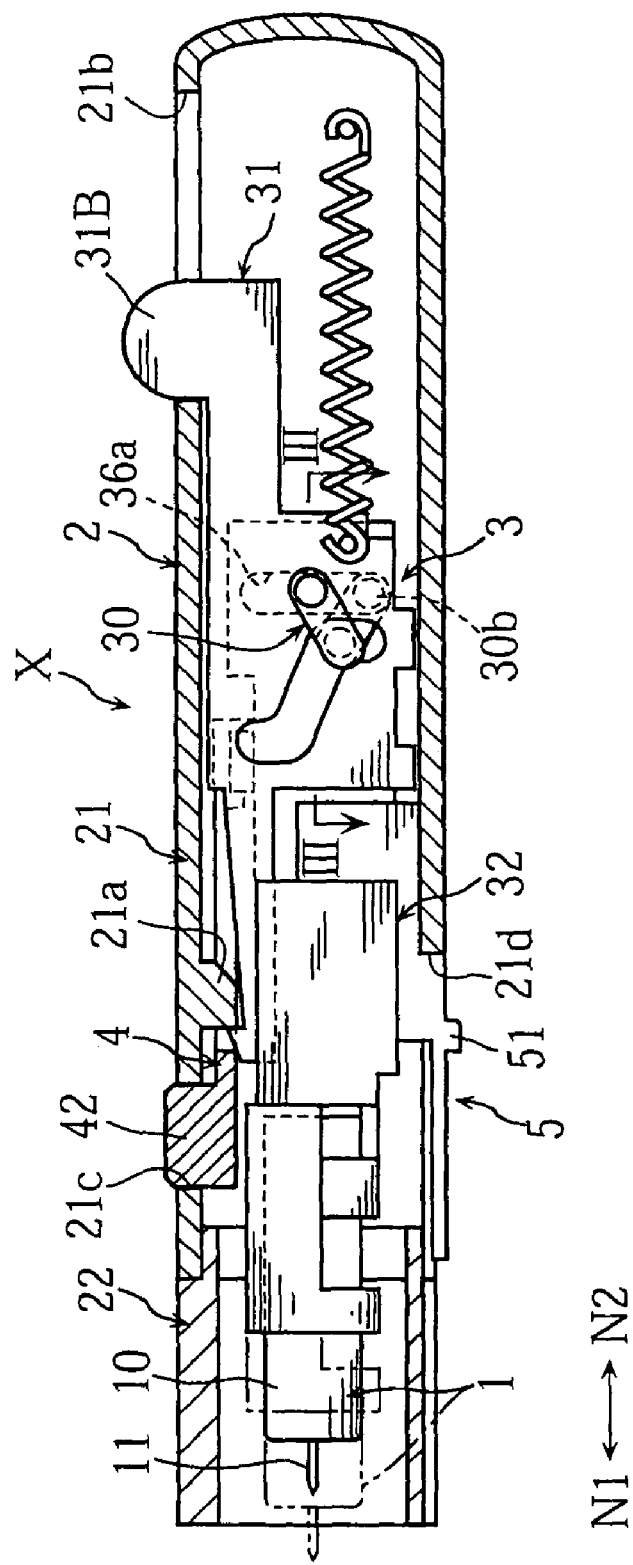
FIG. 1 is a cross-sectional view showing a lancing apparatus according to a first embodiment of the present invention.

First, description is made on the first embodiment of the present invention. A lancing apparatus X shown in FIG. 1 is used for moving a lancet 1 from a standby position (where the lancet 1 is depicted in solid lines in FIG. 1) to a lancing position (where the lancet 1 is depicted in imaginary lines in FIG. 1) so as to stick into a skin to cause bleeding. The lancing apparatus X includes a housing 2, a lancet moving mechanism 3, a latch-release mechanism 4 and a lancet discharge mechanism 5.

The lancet 1, an element that sticks into the skin as noted above, is retained by a lancet holder 32 to be described later, so that it can be moved by the movement of the lancet holder 32. The lancet 1 includes a main body 10 and a needle 11 projecting from the body, and may be used as a disposable item. The main body 10 is made of a resin or the like into a column shape. The needle 11, made of a metal for example, is insert-molded in the main body 10.

The housing 2 provides a space that accommodates various components, and includes a first and a second sleeves 21, 22.

The first sleeve 21 is formed with a protrusion 21a and a first to a third openings 21b to 21d. The protrusion 21a is engageable with a moving plate 31 of the lancet moving mechanism 3 for holding it in place. The first opening 21b permits an operating knob 31B of the moving plate 31 to move through it. The second opening 21c permits a movement of a release button 42 of the latch-release mechanism 4 to be described. The third opening 21d permits a movement of a manipulating portion 51 of the lancet discharge mechanism 5 to be described.

The second sleeve 22 is open at both ends so as to allow the lancet holder 32 to move. The second sleeve 22 can be removably attached to a tip portion of the first sleeve 21, a shown in FIGS. 1 and 2. Accordingly in the lancing apparatus X, the lancet 1 can be easily loaded on the lancet holder 32 when the second sleeve 22 is removed from the first sleeve 21.

Figure 3:
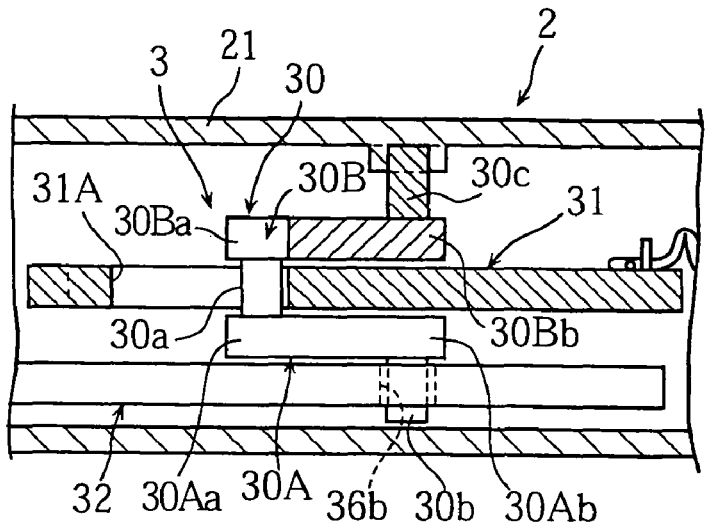
FIG. 3 is a cross-sectional view taken along the line III-III of FIG. 1.

As shown in FIG. 3, the lancet moving mechanism 3 includes a link unit 30, the moving plate 31, and the lancet holder 32. The lancet moving mechanism 3 serves to convert a reciprocating motion of the moving plate 31 into a reciprocating motion of the lancet holder 32 via a circular motion of the link unit 30.

Figure 4:
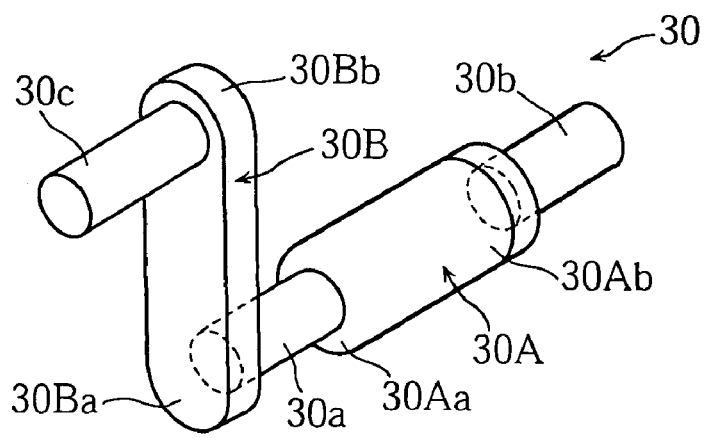
FIG. 4 is a perspective view showing a link unit employed in the lancing apparatus shown in FIG. 1.

Referring to FIGS. 3 and 4, the link unit 30 causes the lancet holder 32 to move as the moving plate 31 moves. The link unit 30 includes a first movable pin 30a, a second movable pin 30b, a fixed pin 30c, a first arm 30A and a second arm 30B.

The first movable pin 30a is engaged with the moving plate 31, and also serves to connect the first and the second arms 30A, 30B. Specifically, the first movable pin 30a is connected with the first and the second arms 30A, 30B at the respective end portions 30Aa, 30Ba, such that the other end portions 30Ab, 30Bb of the first and the second arms 30A, 30B are offset from each other.

The second movable pin 30b, which is engaged with the lancet holder 32, is disposed so as to project in the opposite direction to the first movable pin 30a, from the end portion 30Ab of the first arm 30A.

The fixed pin 30c is disposed so as to project from the end portion 30Bb of the second arm 30B in the opposite direction to the first movable pin 30a, to serve to pivotally fix the link unit 30 to the housing 2.

Figure 5:
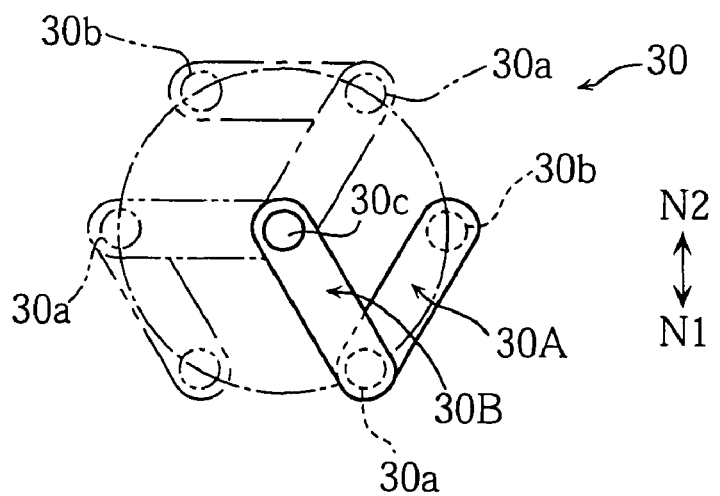
FIG. 5 is a front view showing the link unit, for explaining an operation thereof.

In the link unit 30, since the pins 30a to 30c are mutually linked via the first and the second arms 30A, 30B as shown in FIG. 5, the positional relation among the pins 30a to 30c is fixed. Specifically, the first and the second movable pins 30a, 30b are equally spaced from the fixed pin 30c, while the second movable pin 30b is shifted by 45 degrees with respect to the first movable pin 30a on a circular plane with the fixed pin 30c as the center. Accordingly, rotating the link unit 30 around the fixed pin 30c causes the first and the second movable pins 30a, 30b to make a circular motion around the fixed pin 30c, and the first and the second movable pins 30a-30b, as viewed in a lancing direction and a retreating direction N1-N2, constitute sine waves, the phases of which are shifted by 45 degrees from each other.

The moving plate 31, which is movable with respect to the housing 2 in the lancing direction N1 and the retreating direction N2 as shown in FIGS. 6A and 6B, is connected to the housing 2 via a coil spring Sp. The moving plate 31 is formed with a slot 31A, an operating knob 31B and a hook portion 31C.

The slot 31A permits the movement of the first movable pin 30a of the link unit 30 (see FIG. 3). The slot 31A includes an inclined portion 31Aa obliquely extending with respect to the lancing and the retreating directions N1, N2, and straight portions 31Ab connected respectively to the end portions of the inclined portion 31Aa. As shown in FIGS. 15A-15D, the first movable pin 30a is caused to move in the inclined portion 31Aa at least when the lancet 1 moves from the standby position to the lancing position, while it is caused to move in the straight portion 31Ab at least when the lancet 1 moves away from the lancing position in the retreating direction N2.

With the slot 31a thus formed, the position of the moving plate 31 inside the housing 2 is determined by two positions, i.e., an absolute position of the first movable pin 30a as viewed in the lancing and retreating directions N1-N2 and a relative position of the first movable pin 30a as viewed in the slot 31A. More specifically, the position of the moving plate 31 is determined by the difference between a position of the first movable pin 30a with respect to the fixed pin 30c in the directions N1-N2 and a position of the first movable pin 30a with respect to the center of the slot 31A in the directions N1-N2. Thus, a clockwise rotation of the link unit 30 causes the moving plate 31 to reciprocate between a free position (upper dead point) and a latch position (lower dead point), with the fixed pin 30c set as the center of the operation.

As is understood from FIGS. 6A and 6B, the operating knob 31B is used to manually move the moving plate 31. The operating knob 31B, a portion of which protrudes out of the housing 2 through the first opening 21b, can be moved in the lancing and retreating directions N1, N2 within the first opening 21b.

The hook portion 31C is engaged with the protrusion 21a of the housing 2, so as to latch the moving plate 31 thereon. As is apparent from FIG. 6B, when the coil spring Sp is shrunk the moving plate 31 is positioned such that the hook portion 31C is located behind the protrusion 21a along the retreating direction N2. In contrast, as shown in FIG. 6A, when the hook portion 31C is engaged with the protrusion 21a, the moving plate 31 is biased in the retreating direction N2 by the expanded coil spring Sp.

Figure 7:
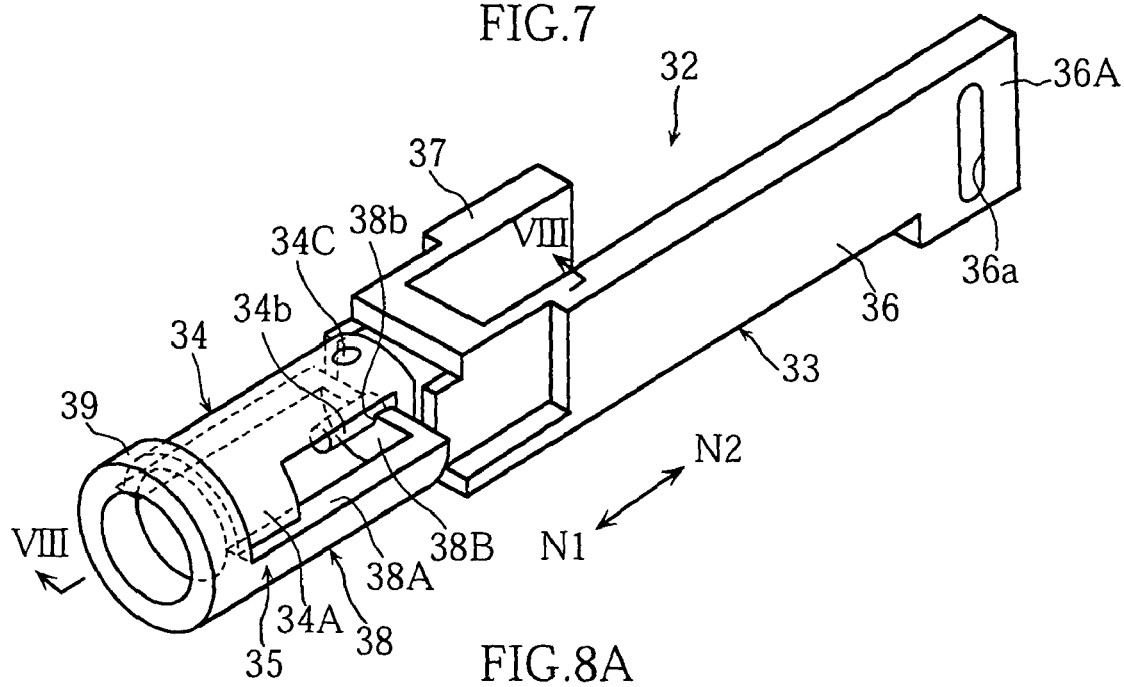
FIG. 7 is a perspective view showing an entire lancet holder employed in the lancing apparatus shown in FIG. 1.
Figure 8A:
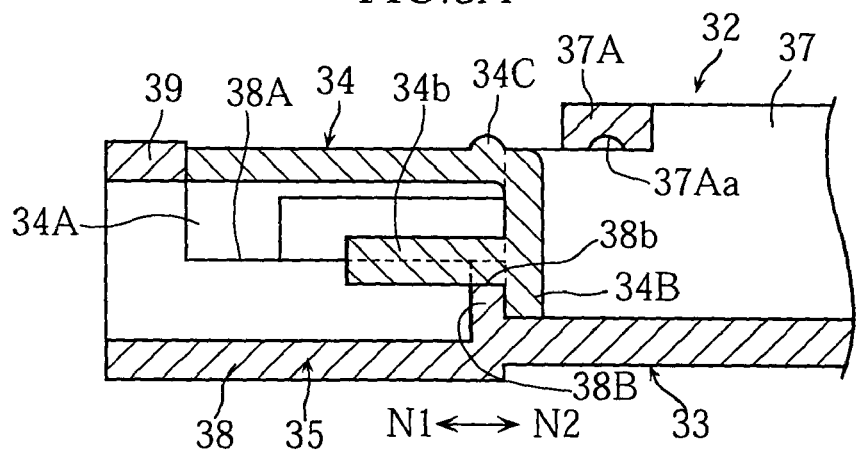
FIGS. 8A and 8B are cross-sectional views taken along the line VIII-VIII of FIG. 7.
Figure 8B:
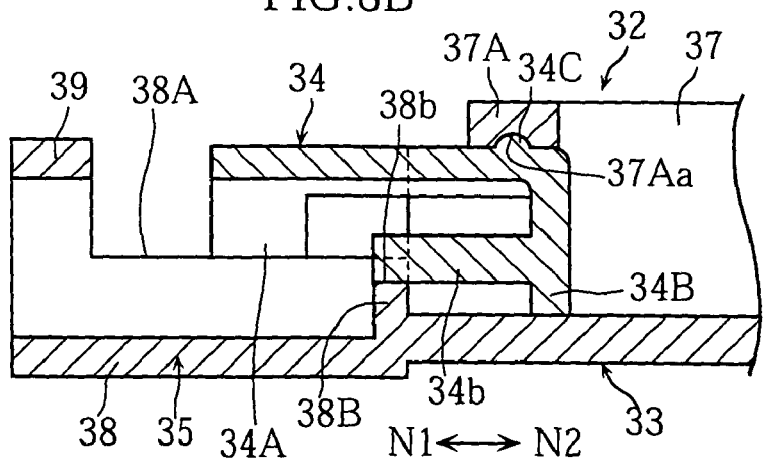

Referring to FIGS. 7, 8A and 8B, the lancet holder 32 serves to retain and move the lancet 1 (see FIG. 1), and is movable in the lancing and retreating directions N1, N2, like the moving plate 31 (see FIGS. 6A and 6B). The lancet holder 32 includes a first and a second members 33, 34 that are relatively movable with respect to each other.

Figure 9:
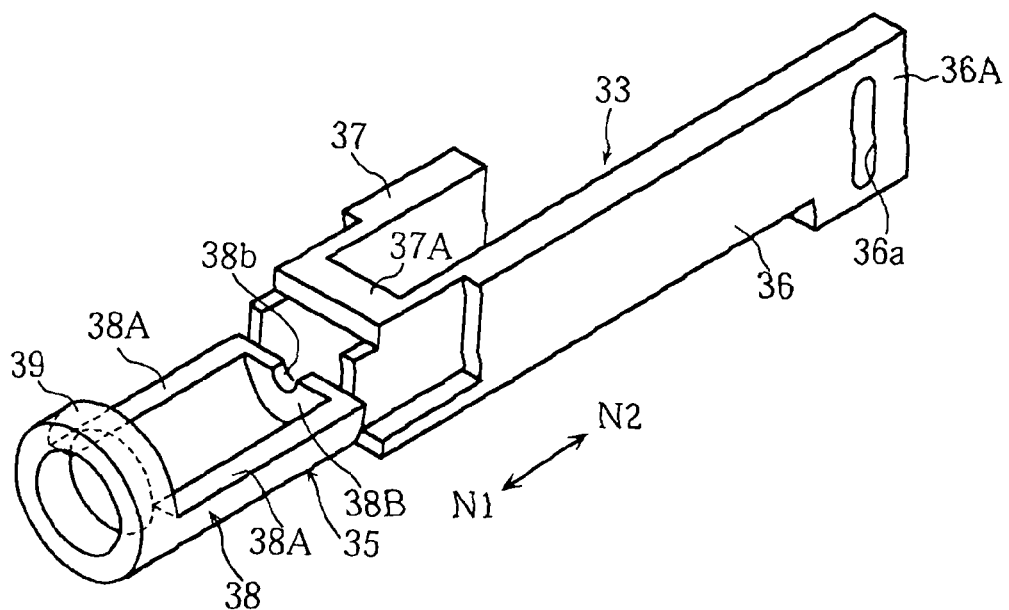
FIG. 9 is a perspective view showing an entire first member of the lancet holder shown in FIG. 7.

The first member 33 includes a holder 35 for retaining the lancet 1 (see FIG. 1), a first plate 36 linked to the moving plate 31 via the link unit 30 (see FIGS. 3 to 5), and a second plate 37 disposed so as to oppose the first plate 36, as shown in FIGS. 7 to 9.

The holder 35 includes a lancet chamber 38 in which the lancet 1 (see FIG. 1) is loaded, and a confining portion 39 that inhibits a radial movement of the lancet 1 (FIG. 1). The lancet chamber 38 is of a semicylindrical shape having an inner surface that fits on the outer surface of the lancet 1, and includes a pair of guide portions 38A and a wall portion 38B. As seen in FIGS. 8A and 8B, the guide portion 38A serves to guide a movement of an arch portion 34 of the second member 34 which will be described later. The wall portion 38B is formed with a cutaway portion 38b. The cutaway portion 38b is formed in a semicircular shape at and end portion of the lancet chamber 38 as shown in FIG. 9, so as to serve to guide a movement of a pin 34b of the second member 34. The confining portion 39 is integrally formed with the holder 35, so as to have an inner diameter that fits on the outer diameter of the lancet 1 (FIG. 1).

The first plate 36 is elongated in the lancing and retreating directions N1, N2, and formed with a slot 36a at an end portion. The slot 36a provides, as seen from FIGS. 1 and 3, room for allowing the second movable pin 30b of the link unit 30 to move, and is orthogonally elongated with respect to the lancing and retreating directions N1, N2. Accordingly, as shown in FIGS. 15A to 15D, the position of the first plate 36 (lancet holder 32) corresponds to the position of the second movable pin 30b in the lancing and retreating directions N1, N2. Consequently, a rotation of the link unit 30 causes the lancet holder 32 to perform a reciprocating movement with the fixed pin 30c as the center of the stroke.

Referring to FIGS. 8A, 8B and 9, the second plate 37 serves to guide the movement of a pushing member 50 (see FIGS. 14A and 14B) of the lancet discharge mechanism 5, in cooperation with the first plate 36. The second plate 37 is connected to the first plate 36 via a bridge portion 37A. The bridge portion 37A includes a recess 37Aa to be engaged with a protrusion 34C of the second member 34.

The second member 34 is moved in the lancing or retreating direction N1 or N2, when loading the lancet 1 (see FIG. 1), by an action of the lancet discharge mechanism 5, as shown in FIGS. 8A and 8B. The second member 34 includes an arch portion 34A and a stopper 34B.

Figure 10:
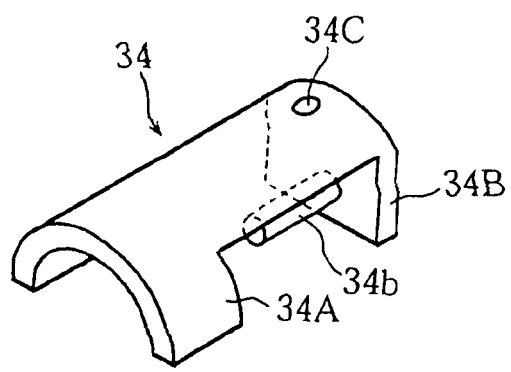
FIG. 10 is a perspective view showing an entire second member of the lancet holder shown in FIG. 7.

Referring to FIG. 10, the arch portion 34A is semicylindrical so as to cover the outer surface of the lancet 1 (see FIG. 1), and is bridged over the guide portion 38A of the first member 33, as shown in FIGS. 7, 8A and 8B.

Referring to FIGS. 8A and 8B, the stopper 34B is butted to the wall portion 38B of the first member 33 when the second member 34 relatively moves with respect to the first member 33 in the lancing direction N1, thus to limit the relative movement of the second member 34 with respect to the first member 33 in the lancing direction N1. The stopper 34B includes a pin 34b projecting in the lancing direction N1. The pin 34b is butted to the lancet 1 (see FIG. 1) when loading the lancet 1 in the lancet holder 32, and is moved through the cutaway portion 38b in the wall portion 38B of the first member 33.

The second member 34 includes a semispherical protrusion 34C located close to the stopper 34B. The protrusion 34C, which is fitted to the recess 37Aa in the bridge portion 37A of the first member 33, is slightly larger in dimension than the recess 37Aa. The protrusion 34C is located so as to be fitted to the recess 37Aa when the lancet 1 is inserted so deeply as to be butted to the wall portion 38B of the first member 33. In this state, since the protrusion 34C is slightly larger in dimensions than the recess 37Aa, the arch portion 34A is caused to apply a pressing force to the lancet 1. Accordingly, when the protrusion 34C is fitted to the recess 37Aa, the arch portion 34A and the lancet chamber 38 hold the lancet 1 (see FIG. 1) therebetween, with the pressing force being applied to the lancet 1. This allows the lancet holder 32 to retain the lancet 1 (see FIG. 1) securely. In contrast, when the protrusion 34C is disengaged with the recess 37Aa, the arch portion 34A only applies a smaller pressing force to the lancet 1 (see FIG. 1), thereby making it easier to remove the lancet 1 from the lancet holder 32.

Figure 11:
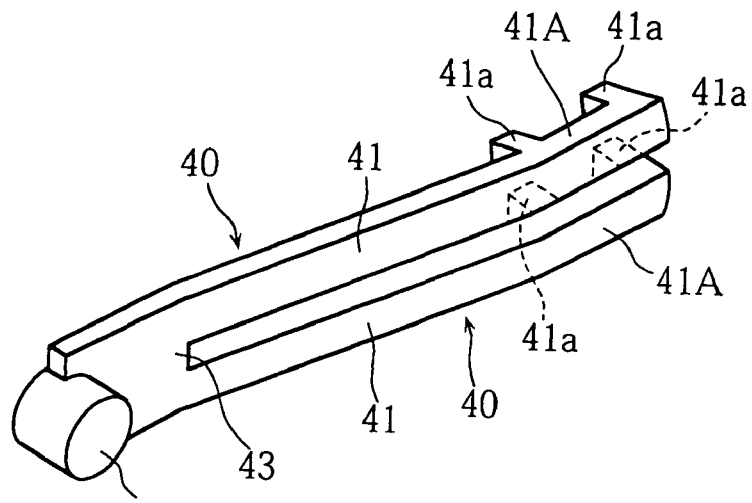
FIG. 11 is a perspective view showing an entire swinging member of a latch-release mechanism employed in the lancing apparatus shown in FIG. 1.

As shown in FIGS. 6A and 6B, the latch-release mechanism 4, which serves to unlatch the moving plate 31 from the housing 2, includes a swinging member 40. The swinging member 40 includes, as shown in FIG. 11, a pair of spring portions 41, a release button 42 and a working portion 43.

Figure 12:
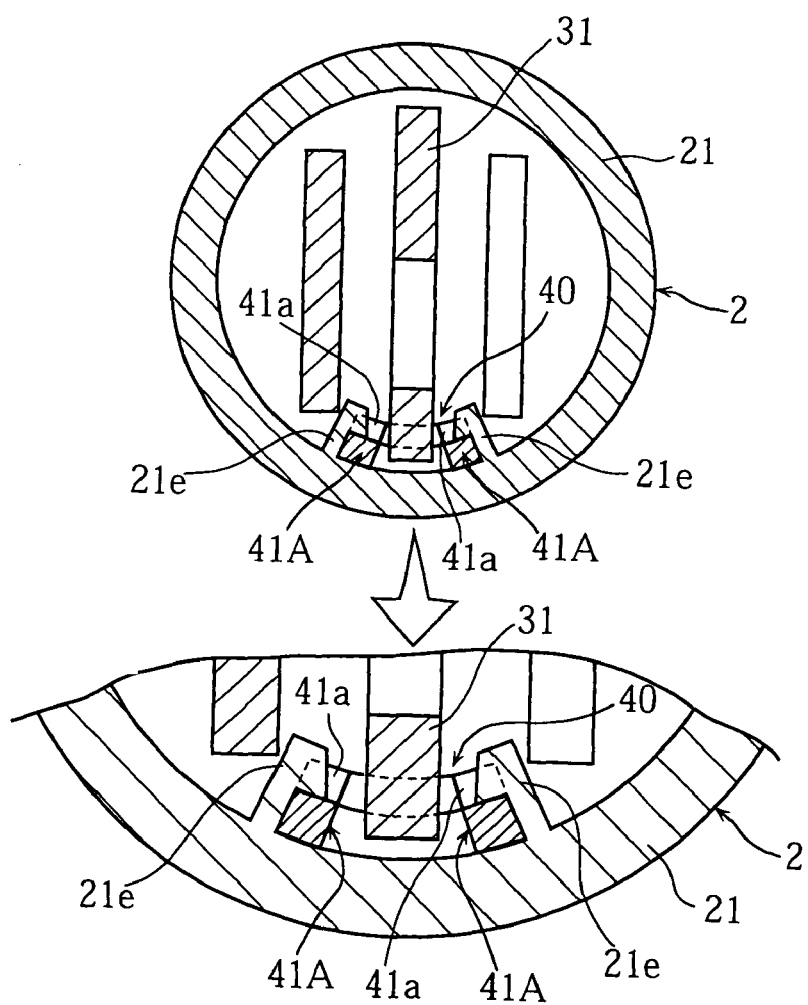
FIG. 12 includes a cross-sectional view and an enlarged fragmentary cross-sectional view showing the swinging member, for explaining a fixing method thereof.

The pair of spring portions 41 has an appropriate elasticity and is extending from the working portion 43. As is seen from FIGS. 11 and 12, the pair of spring portions 41 are spaced from each other so as to allow the hook portion 31C (see FIGS. 6A and 6B) of the moving plate 31 to move through between the spring portions 41. The spring portions 41 respectively include a fixing portion 41A. The fixing portion 41A serves to fix the swinging member 40 to the housing 2. The fixing portion 41A includes a pair of rib portions 41a, between which an engaging piece 21e provided on the first sleeve 21 of the housing 2 is engaged.

Figure 13A:
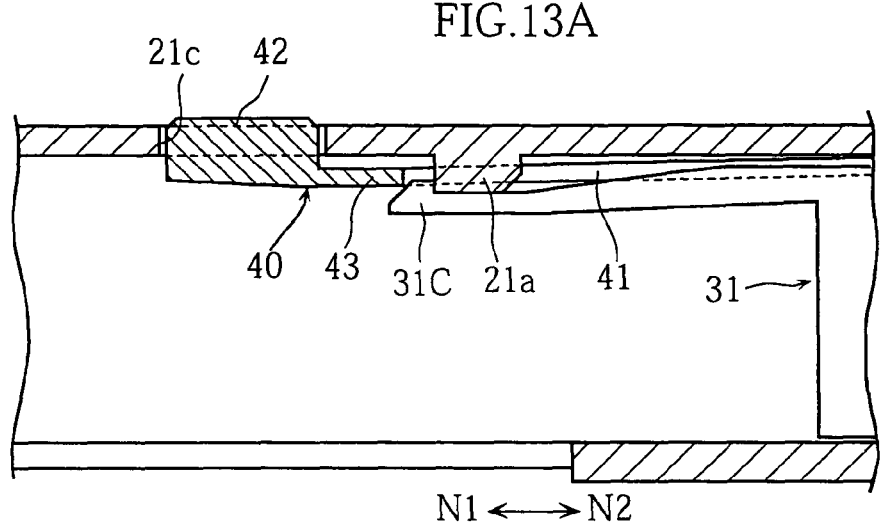
FIGS. 13A to 13C are simplified cross-sectional views of the lancing apparatus shown in FIG. 1, for explaining an operation of the latch-release mechanism.
Figure 13B:
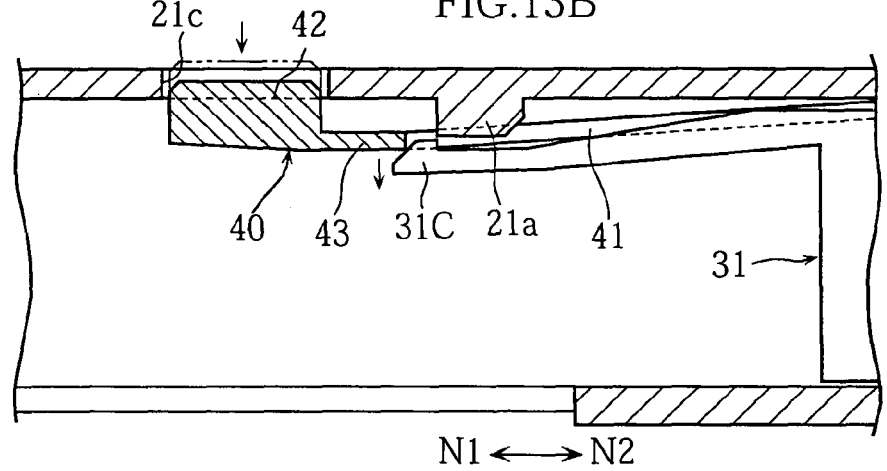
Figure 13C:
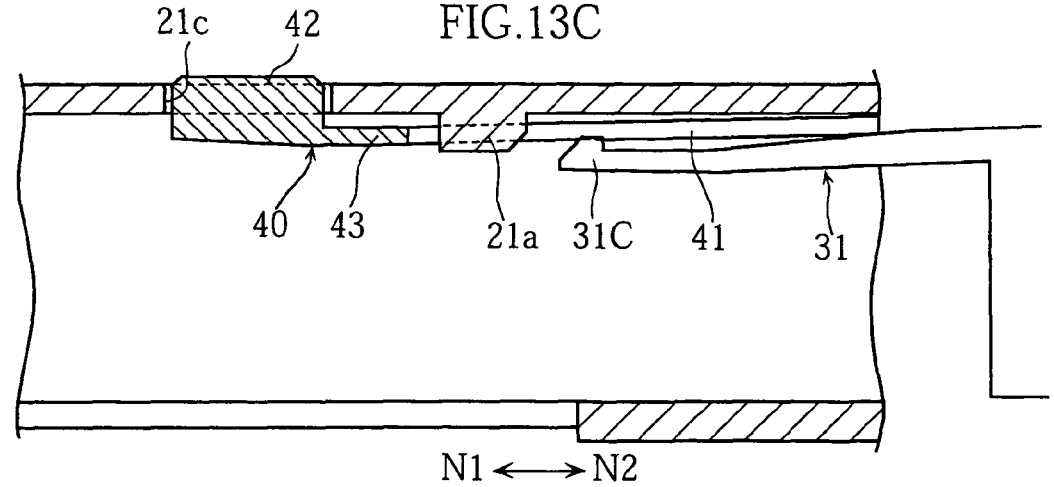

The release button 42 is provided for a user to press down, and the pressing of the release button 42 unlatches the hook portion 31C of the moving plate 31, as shown in FIGS. 13A to 13C. The release button 42 is exposed via the second opening 21c of the housing 2, and movable within the second opening 21c. The release button 42 can swing together with the working portion 43 with the fixing portion 41A set as a fulcrum, since the swinging member 40 is fixed to the housing 2 via the fixing portion 41A (see FIG. 12), and the spring portions 41 have an appropriate elasticity.

The working portion 43 serves to apply a pressing force to the hook portion 31C when the release button 42 is pressed down. When such a pressing force is applied, the hook portion 31C is displaced toward an inner region of the housing 2, thus to be disengaged as shown in FIGS. 13B and 13C. As stated above, when the hook portion 31C is latched on the protrusion 21a, the moving plate 31 is biased in the retreating direction N2. Accordingly, the unlatching of the hook portion 31C causes the moving plate 31 to move in the retreating direction N2, as shown in FIG. 6B.

Figure 14A:
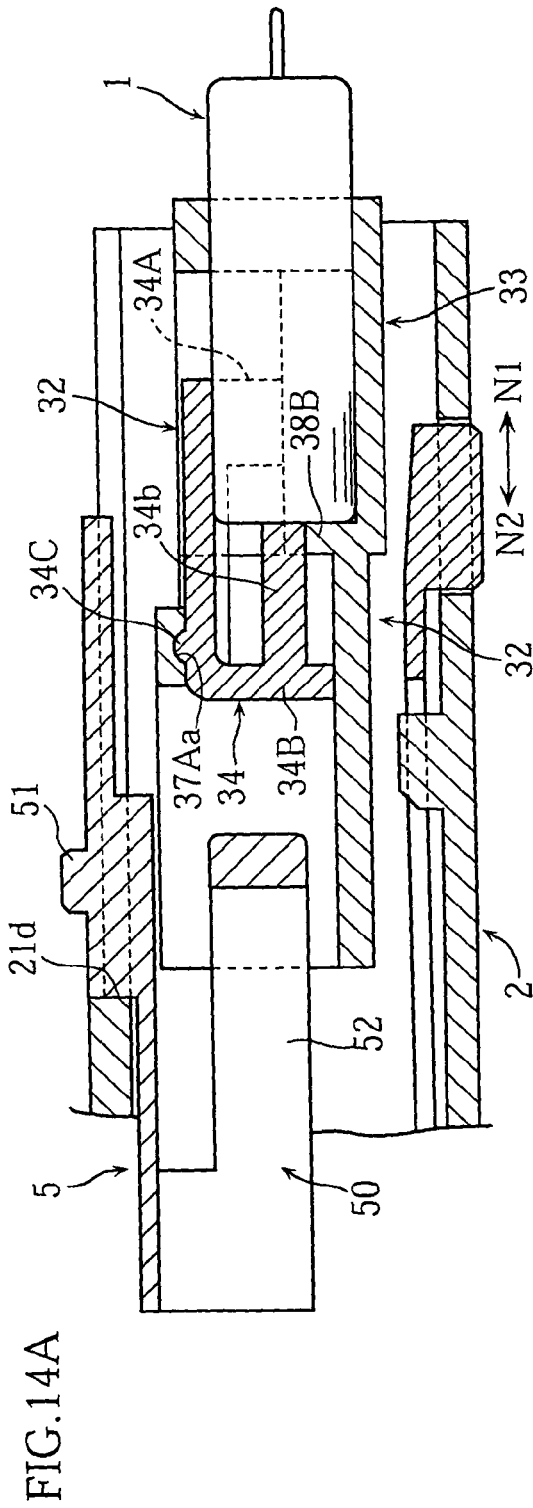
FIGS. 14A and 14B are fragmentary cross-sectional views of the lancing apparatus shown in FIG. 1, for explaining a lancet discharge mechanism employed therein.
Figure 14B:
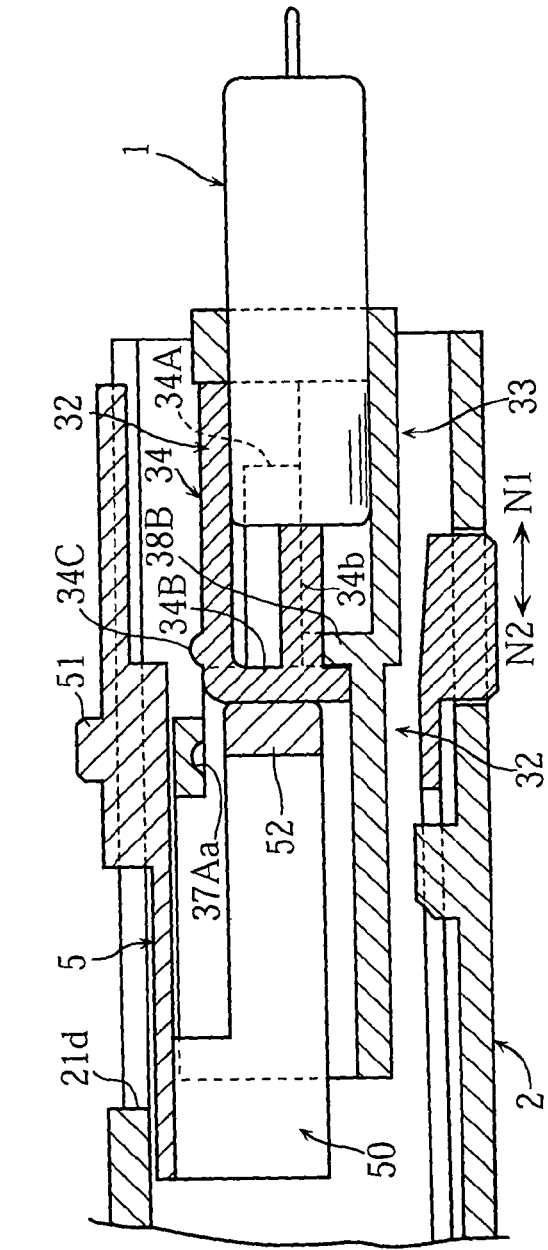

Referring to FIGS. 14A and 14B, the lancet discharge mechanism 5 serves to remove the lancet 1 from the lancet holder 32 after the lancing action. The lancet discharge mechanism 5 includes a pushing member 50 relatively movable with respect to the housing 2 and the lancet holder 32 in the lancing and retreating directions N1, N2. The pushing member 50 includes an operating portion 51 and a working portion 52. The operating portion 51 is manually utilized by a user for moving the pushing member 50, and movable in the lancing and retreating directions N1, N2 within the third opening 21d. The working portion 52 is butted to the stopper 34B of the second member 34 in the lancet holder 32. The working portion 52 is moved in the lancing direction N1 between the first and the second plates 36, 37 when the operating portion 51 is moved in the lancing direction N1. Accordingly, in the lancet discharge mechanism 5, moving the operating portion 51 in the lancing direction N1 causes the working portion 52 to move in the lancing direction N1, to move the second member 34 of the lancet holder 32. The movement of the second member 34 thus caused makes the pin 34b of the second member 34 move in the lancing direction N1, to cause the lancet 1 to move in the lancing direction N1.

The usage of the lancing apparatus X and its principle of operation will now be described. It should be noted here that FIG. 15A shows an "initial state" in which: the moving plate 31 is located at a free position (upper dead point) in the retreating direction N2; the first movable pin 30a is at the left end portion of the inclined portion 31Aa in the slot 31A of the moving plate 31; and the second movable pin 30b is at the left end portion of the slot 36a of the lancet holder 32.

When lancing a skin with the lancing apparatus X, firstly the hook portion 31C of the moving plate 31 is engaged with the protrusion 21a of the housing 2 ("latch state"), and then the lancet 1 is loaded in the lancet holder 32, as shown in FIGS. 1 and 15C. Alternatively, the lancet 1 may be loaded in the lancet holder 32 before the moving plate 31 is latched on the housing 2.

The latch state can be achieved by moving the operating knob 31B of the moving plate 31 in the lancing direction N1, as shown in FIGS. 15A to 15C.

When the moving plate 31 is moved in the lancing direction N1 in the state shown in FIG. 15A, the link unit 30 as a whole, including the second movable pin 30b, rotates clockwise around the fixed pin 30c as shown in FIGS. 15A and 15B, so that the lancet holder 32 is lifted in the retreating direction N2. When the moving plate 31 is moved farther in the lancing direction N1 in the state shown in FIG. 15B, the link unit 30 rotates clockwise further, thereby lowering the lancet holder 32 in the lancing direction N1, as shown in FIG. 15C. This causes the coil spring Sp to expand, and hence the moving plate 31 is biased in the retreating direction N2. In this state, the hook portion 31C of the moving plate 31 comes into engagement with the protrusion 21a of the housing 2.

Figure 2:
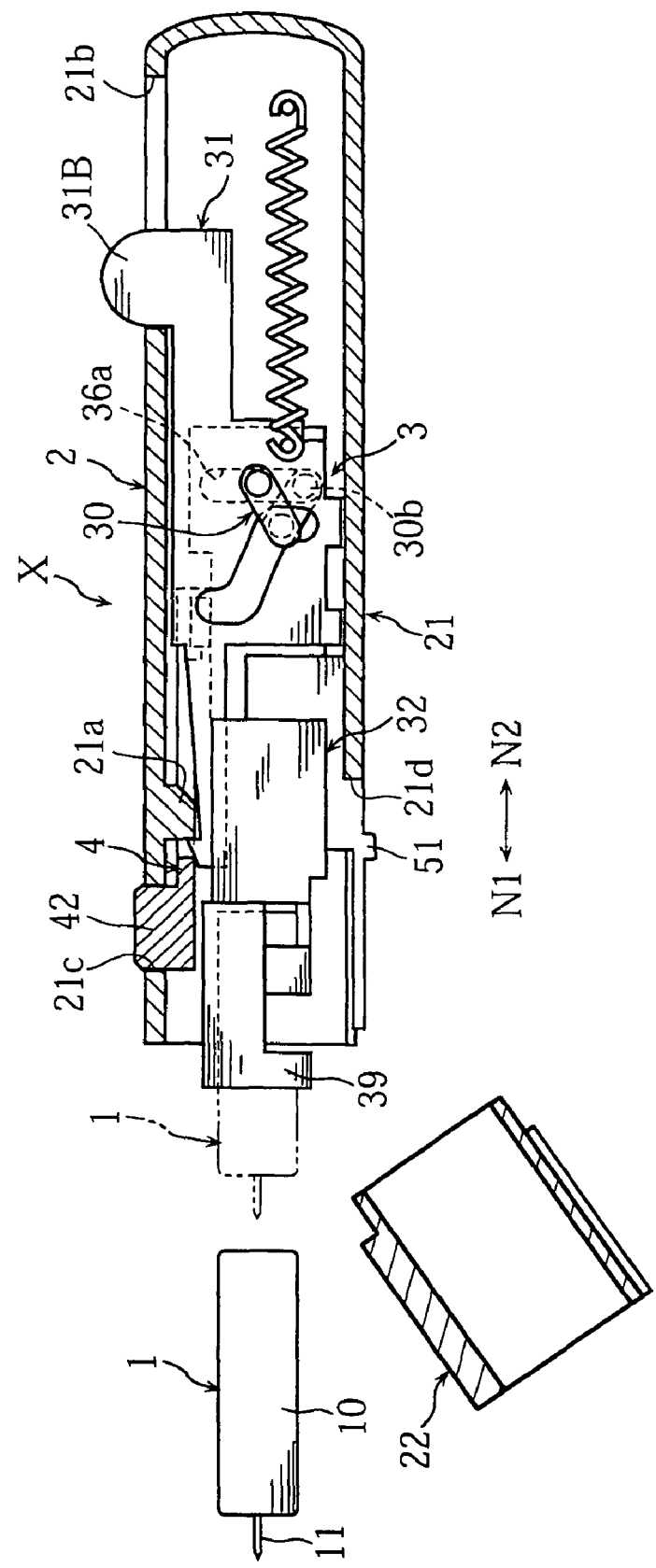
FIG. 2 is a cross-sectional view showing the lancing apparatus of FIG. 1, from which a second sleeve and a lancet are removed.

In first loading the lancet 1, on the other hand, the second sleeve 22 is removed from the first sleeve 21, so as to expose the confining portion 39 of the lancet holder 32 as shown in FIG. 2. Then the end portion of the lancet 1 opposite to the needle is inserted through the confining portion 39. When the lancet 1 is fully inserted, the end face of the lancet 1 is butted to the pin 34 of the second member 34, so that the second member 34 moves in the retreating direction N2 together with the pushing member 50 of the lancet discharge mechanism 5, as shown in FIG. 14B. Once the second member 34 has moved over a predetermined distance, the end face of the lancet 1 is butted to the wall portion 38B of the first member 33, so that the lancet 1 is inhibited from moving further in the retreating direction N2. At this point, the protrusion 34C of the second member 34 fits with the recess 37Aa of the first member 33. This causes the second member 34 to be pressed against the first member 33, to allow the first and the second members 33, 34 to firmly hold the lancet 1 therebetween, thus assuring the secure retention of the lancet 1 by the lancet holder 32. In addition, the click feeling sensed upon fitting the protrusion 34C with the recess 37Aa clearly notifies the user that the lancet 1 has been duly loaded in position. Such a structure prevents the lancet 1 from being insufficiently inserted and hence from sticking too deeply into the skin, which makes the lancing operation much safer.

After the moving plate 31 has been latched and the lancet 1 has been loaded, the release button 42 of the latch-release mechanism 4 is pressed to cause the lancet 1 to stick into the skin, as shown in FIGS. 6A, 6B and 13A to 13C. When the release button 42 is pressed down, the swinging member 40, including the release button 42 and the working portion 43, is moved toward an inner region of the housing 2 with the fixing portion 41A set as a fulcrum. By such action, the working portion 43 is butted to the hook portion 31C thus to inwardly displace the hook portion 31C, whereby the hook portion 31C is unlatched from the protrusion 21a, as shown in FIG. 13B.

Since the moving plate 31 is biased in the retreating direction N2 in the latch state as stated above, the moving plate 31 moves in the retreating direction N2 when the latch is released, which causes the link unit 30 to rotate clockwise, and thus the lancet holder 32 is pressed down in the lancing direction N1 as shown in FIGS. 15C and 15D. Thereafter the moving plate 31 moves farther in the retreating direction N2, which causes the lancet holder 32 to be lifted in the retreating direction N2, and to return to the free position where the lancet holder 32 was before being latched on the housing 2, as shown in FIG. 15A. Such action causes the lancet 1 to be drawn out of the skin.

When the lancing action has been completed, the lancet 1 is removed from the lancet holder 32. To remove the lancet 1, the lancet discharge mechanism 5 is utilized as shown in FIGS. 14A and 14B. Specifically, the operating portion 51 of the lancet discharge mechanism 5 is moved in the lancing direction N1 to cause the lancet 1 to be removed from the lancet holder 32.

When the operating portion 51 is moved in the lancing direction N1, the working portion 52 also moves in the lancing direction N1, to be butted to the stopper 34B. Moving further the operating portion 51 in the lancing direction N1 applies a force to the stopper 34B in the lancing direction N1, via the working portion 52. When a force of appropriate strength is applied to the stopper 34B, the protrusion 34C of the second member 34 is disengaged from the recess 37Aa of the first member 33, so that the second member 34 is moved in the lancing direction N1. Accordingly, the pin 34b of the second member 34 presses the end face of the lancet 1, so as to move the lancet 1 in the lancing direction N1. Since the protrusion 34C is disengaged from the recess 37Aa at this stage, the arch portion 34A of the second member 34 only applies a small force to the lancet 1, thus allowing the lancet 1 to be easily removed from the lancet holder 32, without applying a great force to the lancet 1.

Figure 16A:
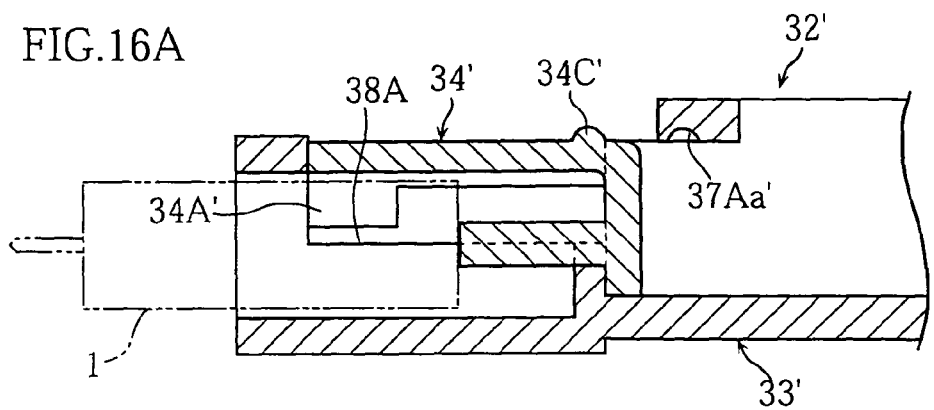
FIGS. 16A to 16D are fragmentary cross-sectional views of the lancet holder, for explaining another operation of the second member.
Figure 16B:
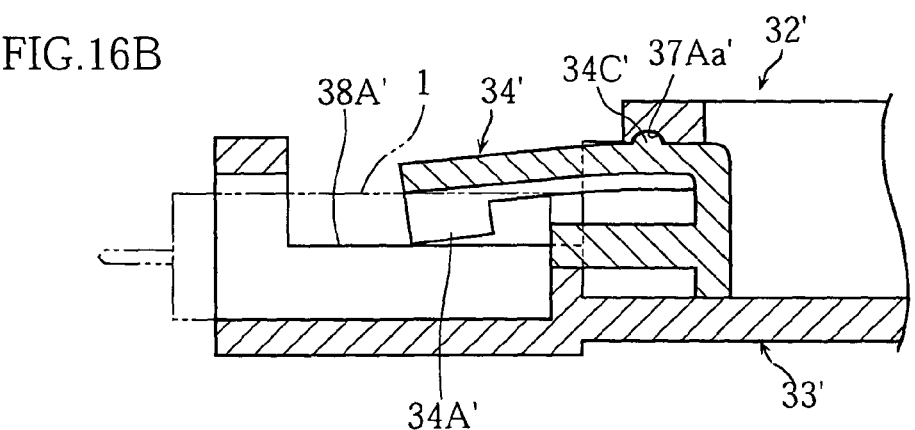
Figure 16C:
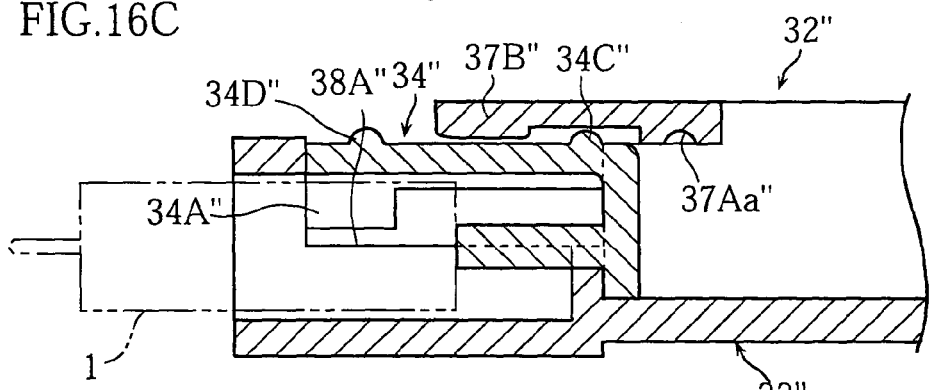
Figure 16D:
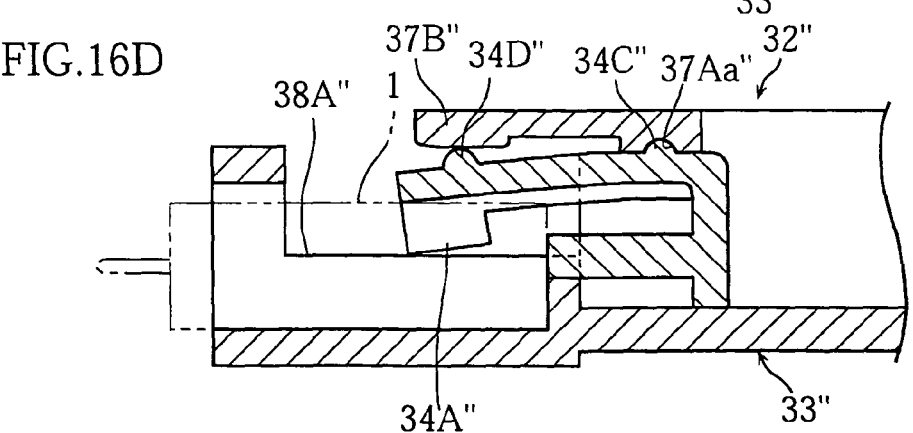

In the lancet holder 32 of the foregoing lancing apparatus X, the arch portion 34A of the second member 34 relatively moves with respect to the guide portion 38A of the first member 33 in close contact therewith, however the lancet can be retained in the lancet holder only if a pressing force is applied to the lancet, for which purpose the arch portion 34A', 34A" of the second member 34', 34" may relatively move with respect to the guide portion 38A', 38A" of the first member 33', 33" with an appropriate spacing, so that the arch portion 34A', 34A" of the second member 34', 34" is inwardly displaced to be pressed against the lancet 1, as shown in FIGS. 16A and 16B or in FIGS. 16C and 16D.

Specifically, in the lancet holder 32' shown in FIGS. 16A and 16B, the protrusion 34C' of the second member 34' is fitted to the recess 37Aa' of the first member 33', so as to inwardly displace the arch portion 34A'.

In contrast, in the lancet holder 32" shown in FIGS. 16C and 16D, another protrusion 34D" is provided on the second member 34" in addition to the protrusion 34C" to be fitted to the recess 37Aa" of the first member 33", and also another protrusion 37B" is provided on the first member 33", so as to be fitted to the protrusion 34D". The protrusion 37B" is inwardly protruding, with its top located at an inner position than the top of the protrusion 34D" of the second member 34". Accordingly, when the second member 34" is relatively moved so as to make access to the first member 33" until the protrusion 34D" of the second member 34" interferes with the protrusion 37B" of the first member 33", the arch portion 34A" of the second member 34" is inwardly displaced.

Figure 17A:
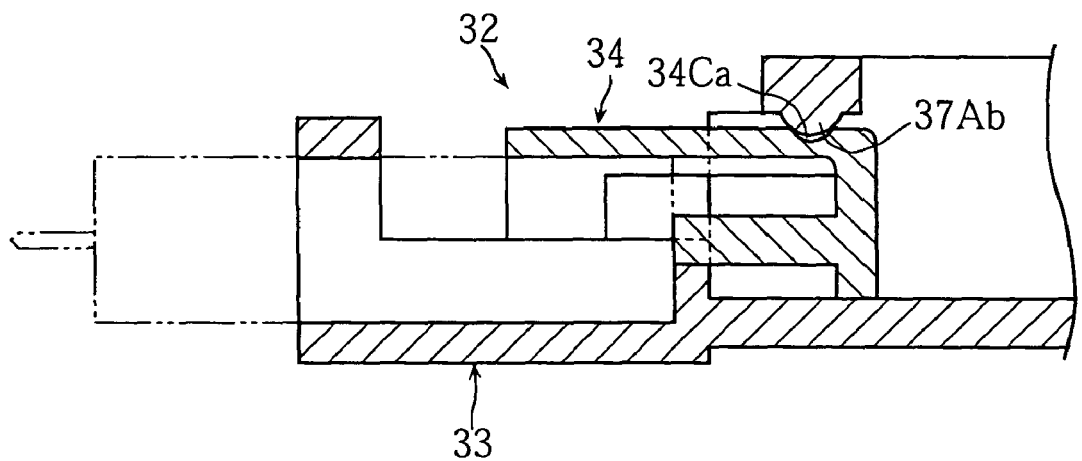
FIGS. 17A to 17C are fragmentary cross-sectional views showing another structure for engaging the second member with the first member in the lancet holder.
Figure 17B:
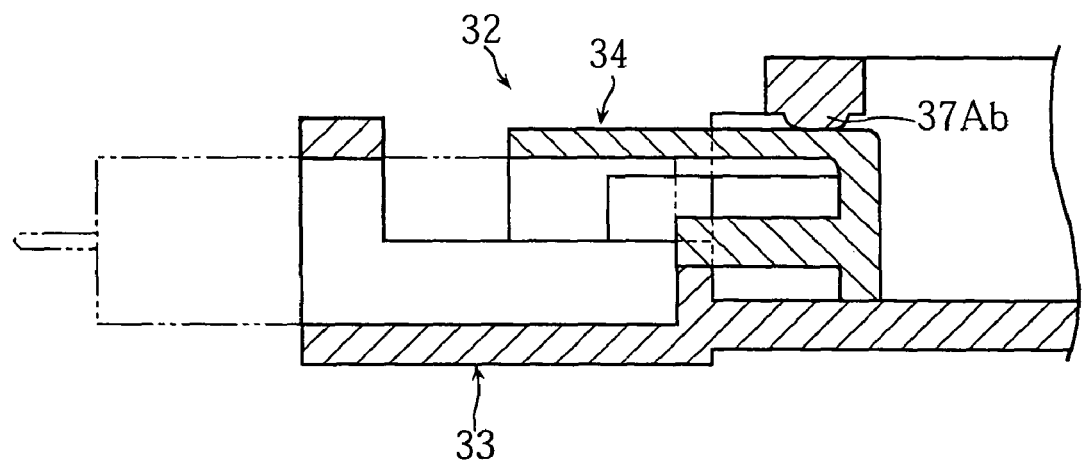
Figure 17C:
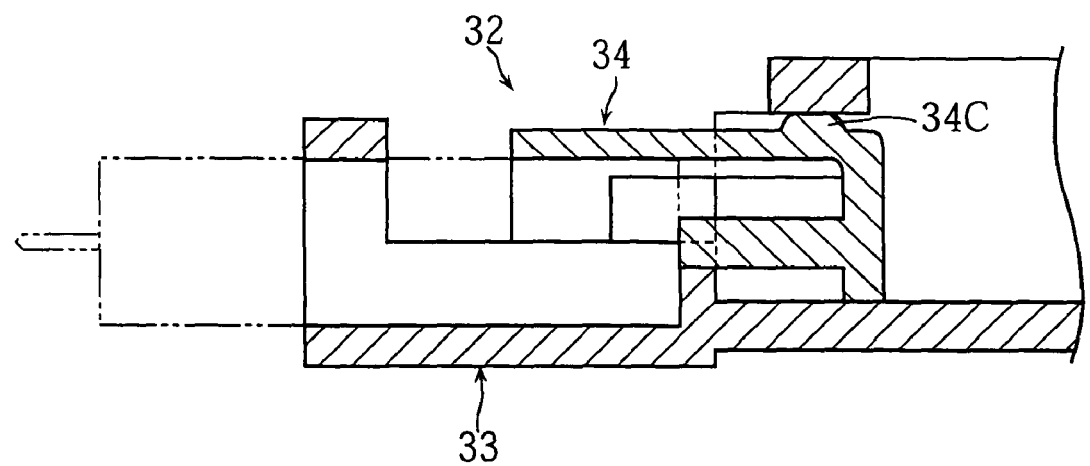
Figure 18A:
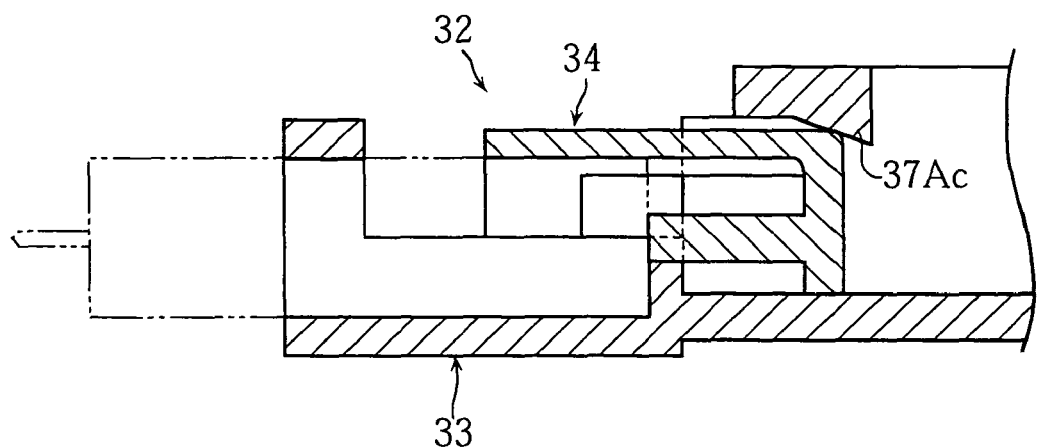
FIGS. 18A and 18B are fragmentary cross-sectional views showing still another structure for engaging the second member with the first member in the lancet holder.
Figure 18B:
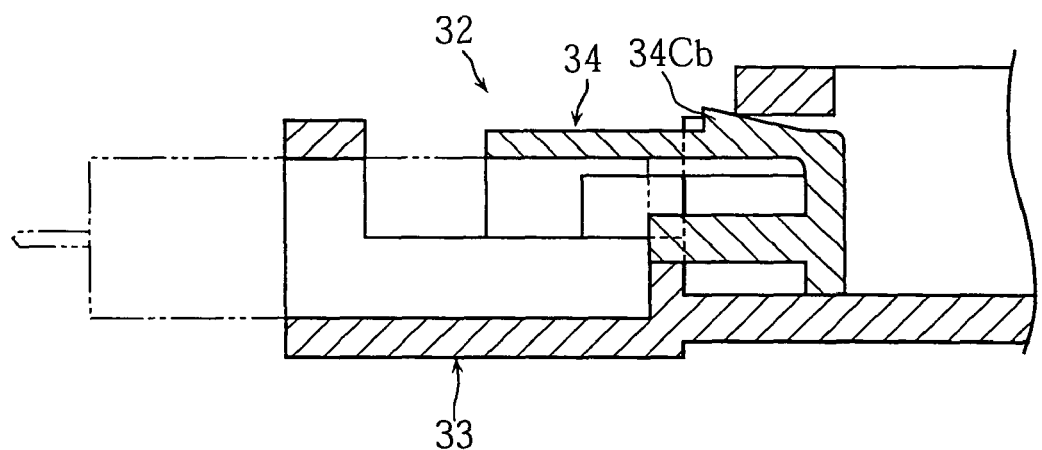

According to the present invention, for engaging the second member of the lancet holder with the first member to cause the second member to apply a pressing force to the lancet, the structure shown in FIGS. 17A to 17C, or in FIGS. 18A and 18B may be employed.

FIG. 17A shows a structure in which the first member 33 of the lancet holder 32 is provided with a semispherical protrusion 37A, while the second member 34 is formed with a recess 34Ca into which the protrusion 37Ab is fitted. In FIG. 17B, the first member 33 of the lancet holder 32 includes a semispherical protrusion 37Ab, and the second member 34 is fixed into the first member 33 and held by the resistance between the protrusion 37Ab and the second member 34. In FIG. 17C, a semispherical protrusion 34C is provided on the second member 34 of the lancet holder 32, and the second member 34 is fixed into the first member 33 and held by the resistance between the protrusion 34C and the first member 33.

In FIG. 18A, the first member 33 of the lancet holder 32 includes a tapered protrusion 37Ac, so that the second member 34 is fixed into the first member 33 and held by the resistance between the protrusion 37Ac and the second member 34. In FIG. 18B, the second member 34 of the lancet holder 32 includes a tapered protrusion 34Cb, so that the second member 34 is fixed into the first member 33 and held by the resistance between the protrusion 34Cb and the first member 33.

Now, a second embodiment of the present invention will be described.

Figure 19A:
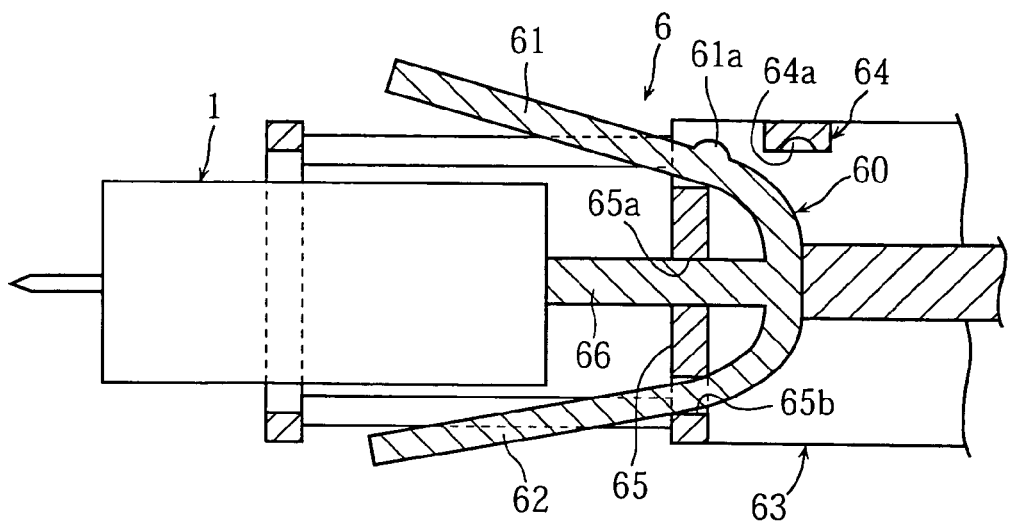
FIGS. 19A and 19B are fragmentary cross-sectional views showing a lancet holder according to a second embodiment of the present invention.
Figure 19B:
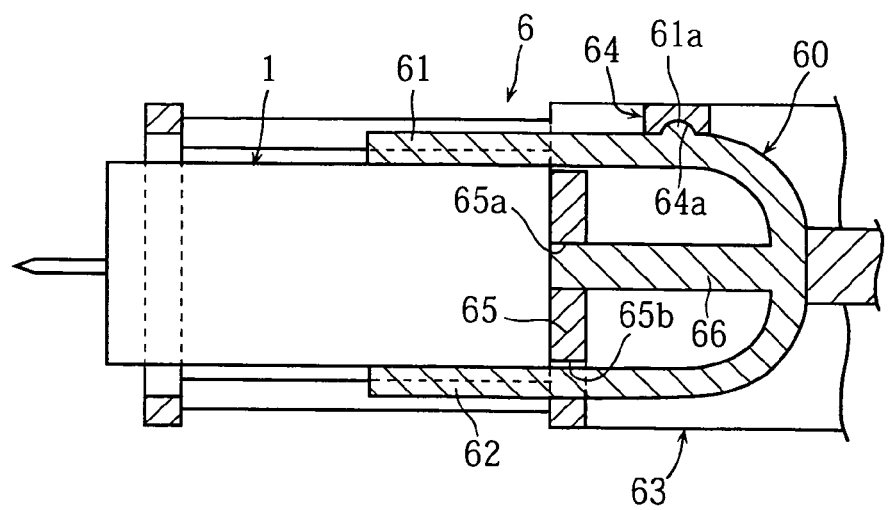

FIGS. 19A and 19B shows a lancet holder 6, in which a second member 60 includes a first and a second flexible portions 61, 62. The first flexible portion 61 includes a protrusion 61a to be fitted into a recess 64a provided on a bridge portion 64 of a first member 63. The first member 63A includes through-holes 65a, 65b located on a wall portion 65, so as to permit a movement of a working portion 66 of the second member 60 and the second flexible portion 62.

As shown in FIG. 19A, the first and the second flexible portions 61, 62 do not touch the lancet 1 when the second member 60 is on the side indicated by the arrow N1, and hence do not apply a pressing force to the lancet 1. In contrast, when the second member 60 is moved in a direction indicated by the arrow N2 from the state of FIG. 19A to the state shown in FIG. 19B, the first flexible portion 61 interferes with the bridge portion 64 thus to be displaced in a direction of accessing the lancet 1, and the second flexible portion 62 interferes with an inner wall of the through-hole 65b thus to be displaced in a direction of accessing the lancet 1. Consequently, the first and the second flexible portions 61, 62 are brought into contact with the lancet 1, thereby applying a pressing force to the lancet 1.

Now, a third embodiment of the present invention will be described.

A lancet holder according to this embodiment can be suitably employed for a lancet 1' shown in FIG. 20A. The lancet 1' is also a general-purpose product like the foregoing lancet 1 (see FIG. 2) having a column-shaped main body 10, and includes a recessed portion 12' on a main body 10'. The lancet 1' includes a stepped portion 13' defined by the recessed portion 12'.

As shown in FIGS. 20B and 20C, a lancet holder 7 is basically similar to the lancet holder 6 (see FIGS. 19A and 19B) according to the third embodiment. A difference in the lancet holder 7 from the lancet holder 6 (see FIGS. 19A and 19B) lies in that a first and a second flexible portions 71, 72 respectively include a protrusion 71b, 72b at en end portion. The protrusions 71b, 72b serve to get engaged with the stepped portion 13' of the lancet 1', as explicitly shown in FIG. 20C.

The lancet holder 7 is unable to apply a pressing force to the lancet 1' when the first and the second flexible portions 71, 72 of a second member 70 are located on the side indicated by the arrow N1. However, when the second member 60 is moved in a direction indicated by the arrow N2 under the state of FIG. 20B thus to present a state as shown in FIG. 20C, the first and the second flexible portions 71, 72 are brought into contact with the lancet 1', thereby applying a pressing force to the lancet 1'. In this state, the protrusions 71b, 72b of the first and the second flexible portions 71, 72 are respectively engaged with the stepped portion 13' of the lancet 1'. Such a structure ensures the secure retention of the lancet 1', by the first and the second flexible portion 71, 72.

While this embodiment represents a case where the general-purpose lancet including the recessed portion 12' is employed, a lancet including a customized recessed portion that fits the protrusions 71b, 72b of the first and the second flexible portions 71, 72 may be produced, for use with the lancet holder 7.

Now, a fourth embodiment of the present invention will be described. This embodiment relates to a modification of the lancet holder.

Figure 21:
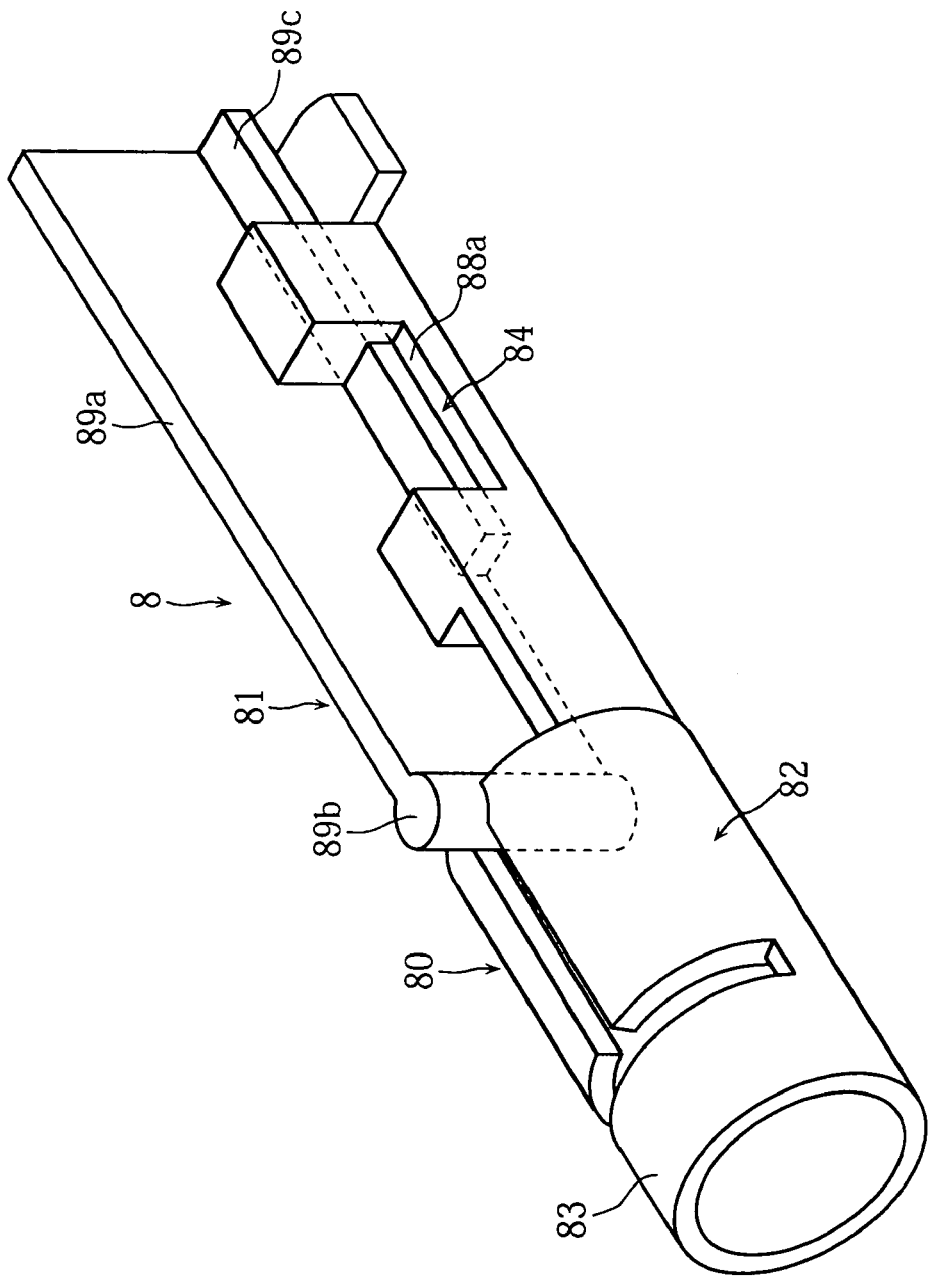
FIG. 21 is a fragmentary perspective view showing a lancet holder according to a fourth embodiment of the present invention.

Referring to FIG. 21, a lancet holder 8 includes a first and a second members 80, 81 relatively movable with respect to each other.

Figure 22:
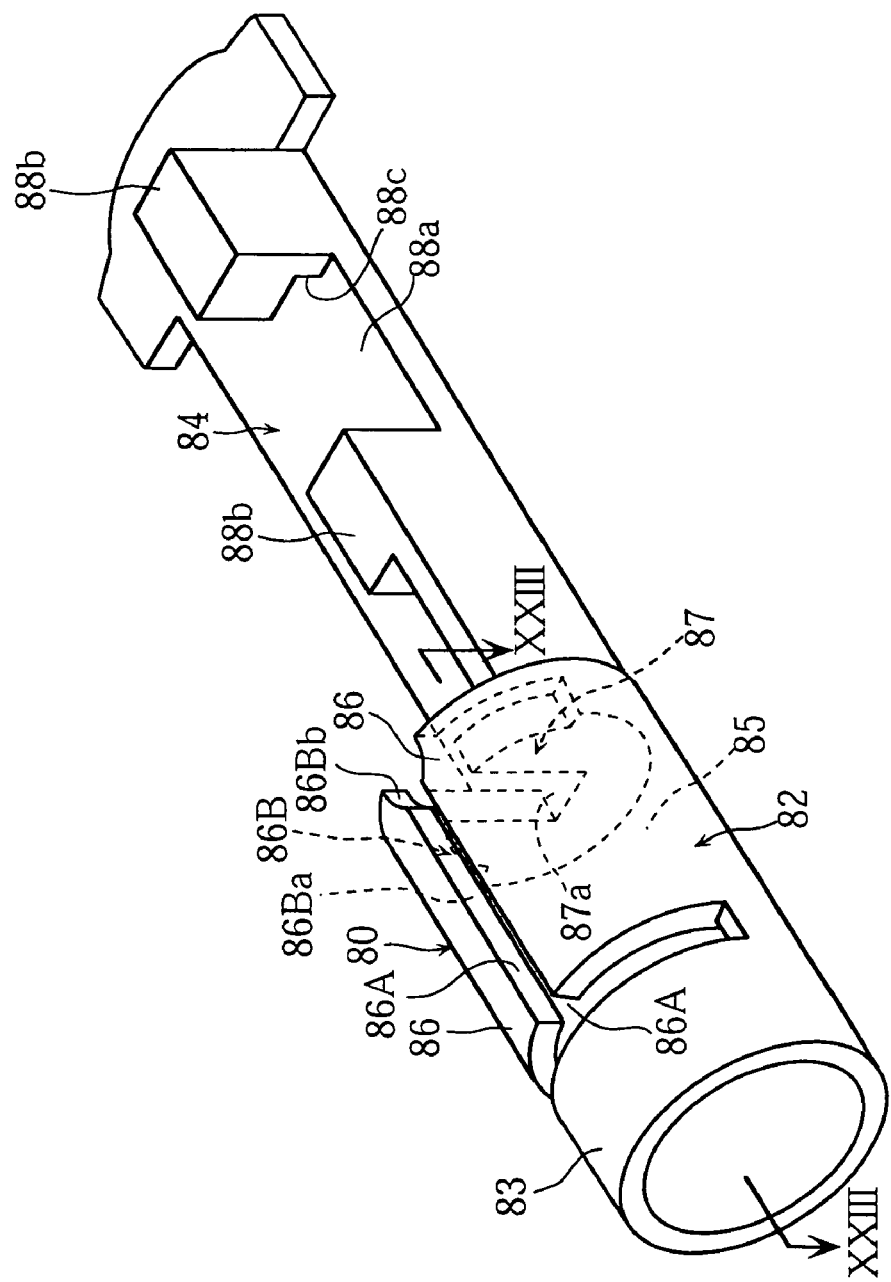
FIG. 22 is a fragmentary perspective view showing a first member of the lancet holder shown in FIG. 21.
Figure 23:
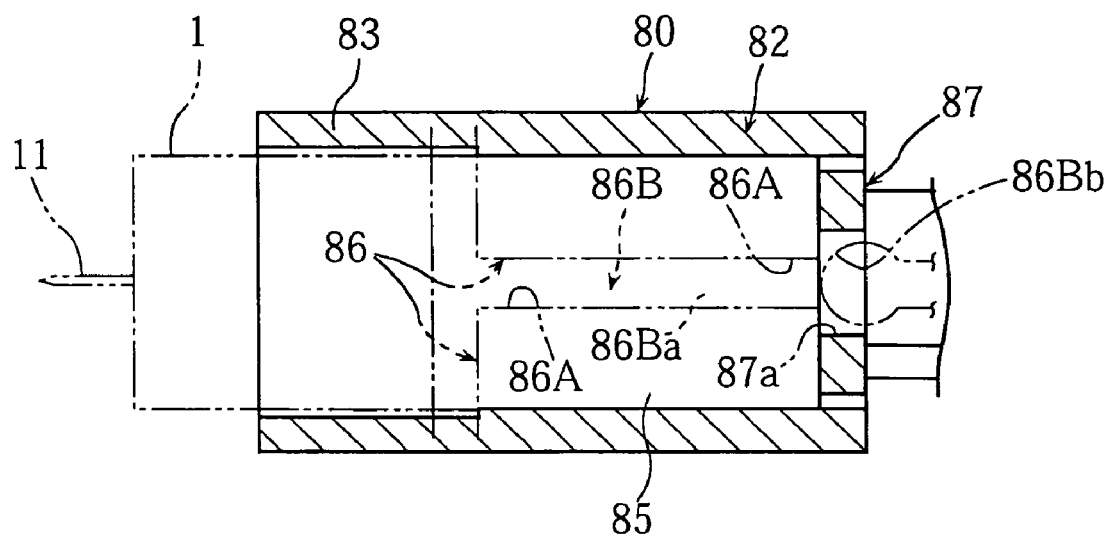
FIG. 23 is a cross-sectional view taken along the line XXIII-XXIII of FIG. 22.

As shown in FIGS. 22 and 23, the first member 80 includes a holder body 82, a confining portion 83 and a guide portion 84.

The holder body 82 has an inner surface that fits on the outer surface of the lancet 1, with an inner diameter equal to or slightly smaller than the outer diameter of the lancet in a natural condition of the holder body 82. The holder body 82 includes a lancet chamber 85, a pair of movable portions 86 and a stopper 87.

The lancet chamber 85 is of a semicylindrical shape. The pair of movable portions 86, which are formed as an extension of the holder body 82 to cover an inner portion of the lancet chamber 85, serve to apply a pressing force to the lancet 1. The movable portions 86 have an arc-shaped inner surface, such that the respective end faces 86A oppose each other across a gap 86B. The gap 86B has a uniform width along its main portion 86Ba, while includes arc-shaped cutaway portions 86Bb at the respective corners of the movable portions 86, thus having a larger width at an end portion thereof. The pair of movable portions 86 can be outwardly displaced by expanding the gap 86B. The stopper 87 can interfere with the end face of the lancet 1 when loading the lancet, thus to inhibit further movement of the lancet 1. The stopper 87 includes a cutaway portion 87a. The cutaway portion 87a serves to guide a movement of a column-shaped portion 89b of the second member 81 to be described later.

The confining portion 83 inhibits a radial movement of the lancet 1. The confining portion 83 constitutes an extension of the holder body 82 in a ring shape, with an inner diameter slightly larger than the outer diameter of the lancet 1 (inner diameter of the holder body 82).

As seen from FIGS. 21 and 22, the guide portion 84 serves to guide a movement of the second member 81, and includes a sliding portion 88a. Two block portions 88b extend from the sliding portion 88a, and a gap 88c is provided between the sliding portion 88a and the respective block portions 88b.

Figure 24:
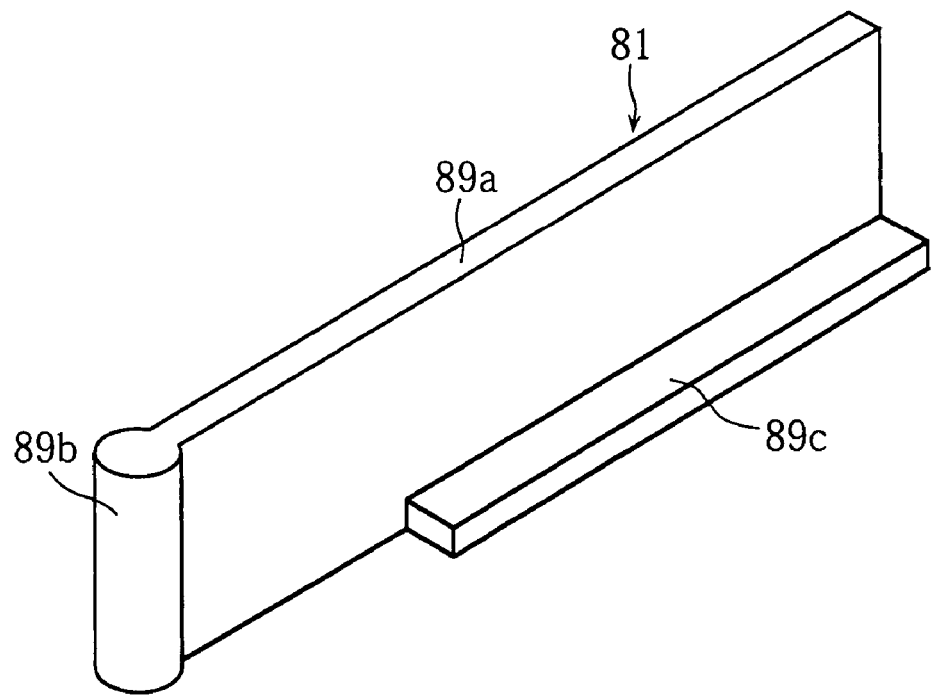
FIG. 24 is a fragmentary perspective view showing a second member of the lancet holder shown in FIG. 21.

As shown in FIGS. 21 and 24, the second member 81 is to be moved in the lancing or retreating direction N1 or N2, along the sliding portion 88a of the first member 80. The second member 81 is made of a plate 89a with a column-shaped portion 89b located at an end portion, and with a flange portion 89c extending from a plate-shape portion.

The column-shaped portion 89b serves to interfere with the lancet 1 and to expand the width of the gap 86B of the first member 80, as seen in FIGS. 25A, 25B, 26A and 26B. The column-shaped portion 89b has a larger diameter than the width of the main portion 86Ba of the gap 86B, and an outer surface that fits on the inner surface of the cutaway portions 86Bb of the first member 80. The flange portion 89c is to be guided by the block portions 88b of the first member 80, so as to move through the gap 88c on the first member 80.

Figure 26A:
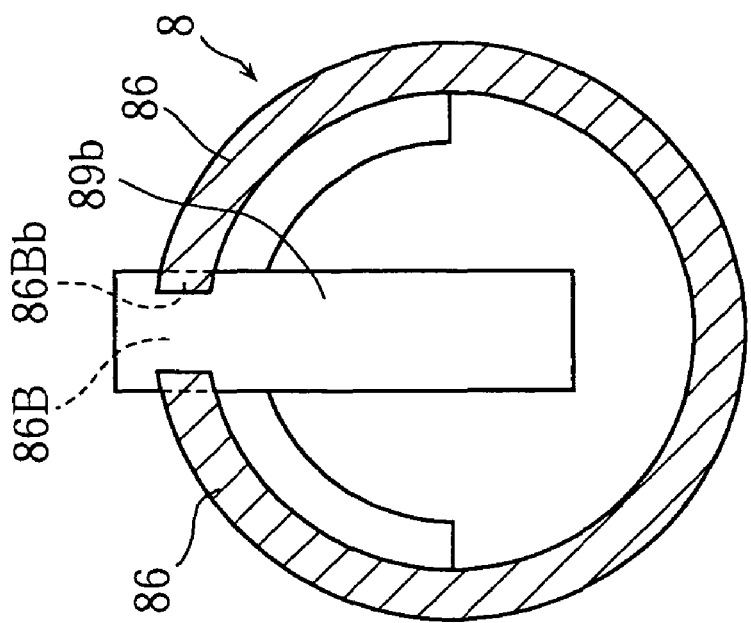
FIG. 26A is a cross-sectional view taken along the line XXVIa-XXVIa of FIG. 25A.
Figure 26B:
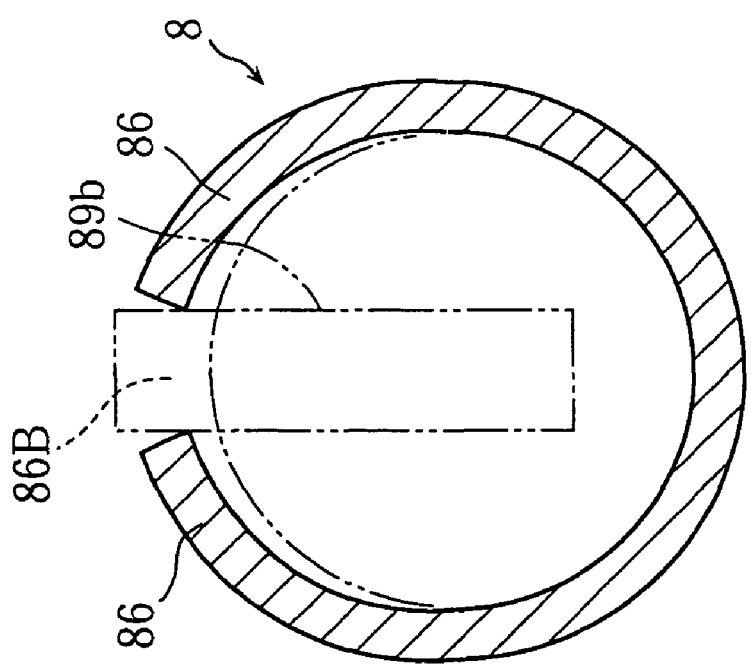
FIG. 26B is a cross-sectional view taken along the line XXVIb-XXVIb of FIG. 25B.

When loading the lancet 1 in the lancet holder 8, an end portion of the lancet 1 opposite to the needle 11 (see FIG. 23) is inserted through the confining portion 83. In the lancet holder 8 at this stage, as shown in FIGS. 25A and 26A, the gap 86B of the first member 80 is expanded since the column-shaped portion 89b of the second member 81 is located in the main portion 86Ba of the gap 86B. When the lancet 1 is inserted by a predetermined depth, the end face of the lancet 1 is butted to the column-shaped portion 89b, so as to move the column-shaped portion 89b in the retreating direction N2 through the main portion 86Ba of the gap 86B. When the lancet 1 has moved over a predetermined distance, the end face of the lancet 1 is butted to the stopper 87 of the first member 80, which inhibits further movement of the lancet 1 in the retreating direction N2, as shown in FIGS. 25B and 26B. At this stage, the column-shaped portion 89b falls in the cutaway portions 86Bb of the first member 80. This causes the movable portions 86 to be inwardly displaced thus to reduce the width of the gap 86B, so that the movable portions 86 of the first member 80 apply a pressing force to the lancet 1. In addition, when the column-shaped portion 89b fits into the cutaway portions 86Bb, the user feels a click, to be assured that the lancet 1 has been properly loaded in the lancet holder 8.

In contrast, the removal of the lancet 1 from the lancet holder 8 is performed by moving the second member 81 in the lancing direction N1. The second member 81 may be moved via the lancet discharge mechanism 5 according to the first embodiment.

Specifically, by moving the column-shaped portion 89b in the lancing direction N1 when the column-shaped portion 89b is fitted in the cutaway portions 86Bb, the column-shaped portion 89b is disengaged and caused to move through the main portion 86Ba of the gap 86B. This expands the main portion 86Ba of the gap 86B by outwardly displacing the movable portions 86, thereby reducing the pressing force so far applied to the lancet 1 by the movable portions 86. This ensures easy removal of the lancet 1 from the lancet holder 8.

The structures of the gap 86 of the first member 80 and the column-shaped portion 89b of the second member 81 are not limited to those described in the foregoing embodiment. For example, the gap 86B has only to include a portion narrower than the diameter of the column-shaped portion 89b, and does not necessarily have to include a cutaway portion.

A fifth embodiment of the present invention will now be described. This embodiment also relates to a modification of the lancet holder.

Figure 27:
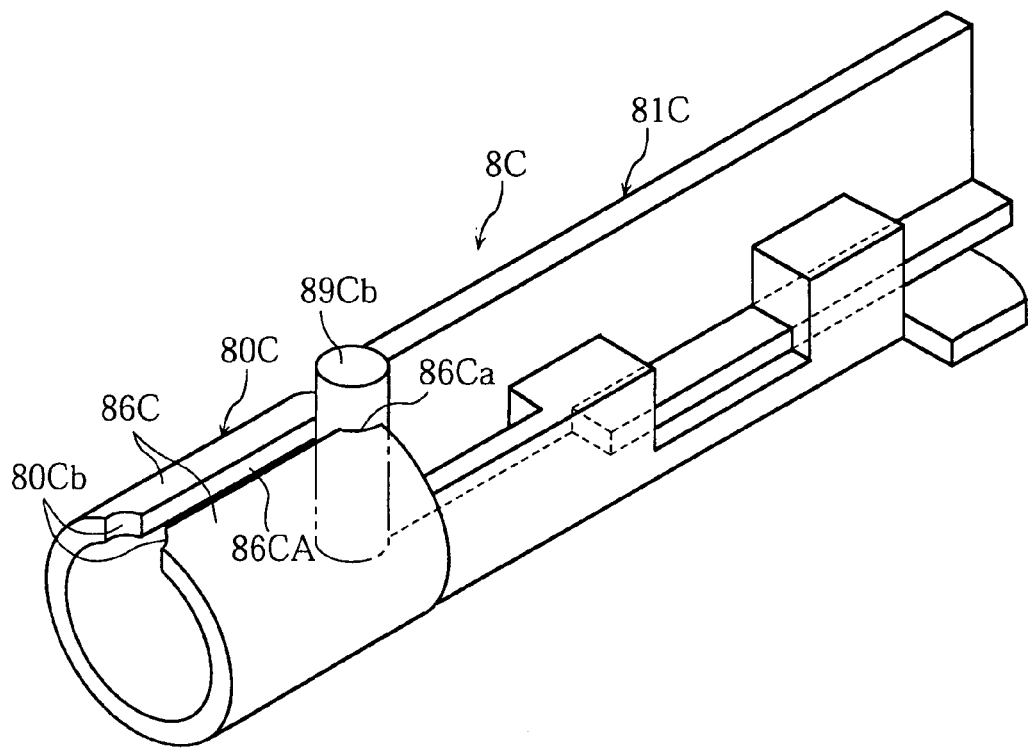
FIG. 27 is a fragmentary perspective view showing a lancet holder according to a fifth embodiment of the present invention.

As shown in FIG. 27, a lancet holder 8C is of a similar shape to the lancet holder 8 according to the fourth embodiment (see FIGS. 21, 22), and includes a first and a second members 80C, 81C relatively movable with respect to each other. In the first member 80C, movable portions 86C respectively include two arc-shaped cutaway portions 86Ca, 86Cb, so that a gap 86CA defined therebetween has a larger width at both end portions. However, the first member 80C does not include the confining portion 83 (see FIGS. 21, 22 and so on) included in the foregoing lancet holder 8. The second member 81C is of generally the same structure as the second member 81 of the lancet holder 8.

The cutaway portions 86Ca of the movable portions 86C have a similar function to that of the cutaway portions 86Bb (see FIGS. 21, 22) of the lancet holder 8. More specifically, the cutaway portions 86Ca are to be engaged with the column-shaped portion 89Cb of the second member 81C, to provide a click feeling when the lancet 1 (see FIGS. 28A to 28C) is fixed in place in the lancet holder 8C. The cutaway portions 86Cb are to be engaged with the column-shaped portion 89Cb when the lancet 1 is discharged from the lancet holder 8. Accordingly, the user recognizes that the lancet 1 (see FIGS. 28A to 28C) has been discharged upon feeling the click when the column-shaped portion 89Cb fits into the cutaway portions 86Cb.

Figure 28:
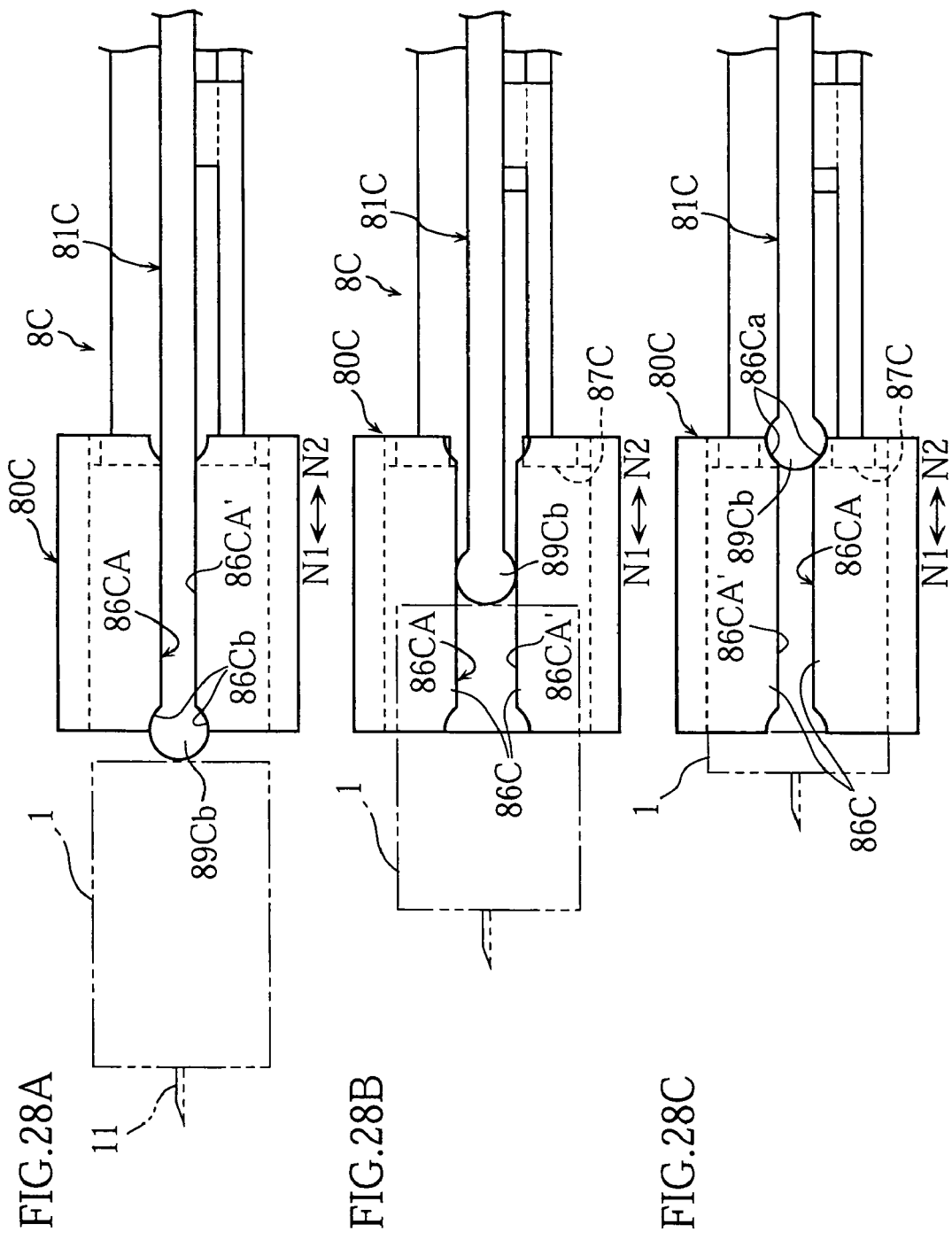
FIGS. 28A and 28C are fragmentary plan views showing the lancet holder shown in FIG. 27.

As shown in FIGS. 28A to 28C, when loading the lancet 1 in the lancet holder 8C, the end portion of the lancet 1 opposite to the needle 11 is inserted, with the column-shaped portion 89Cb of the second member 81C engaged with the cutaway portions 86Cb of the first member 80C. At this moment in the lancet holder 8C, as shown in FIGS. 28A and 28B, the lancet 1 is butted to the column-shaped portion 89Cb so as to move the column-shaped portion 89Cb in the retreating direction N2 through a main portion 86CA' of a gap 86CA. This expands the width of the gap 86CA from the natural state. When the lancet 1 has moved over a predetermined distance, the end face of the lancet 1 is butted to the stopper 87C of the first member 80C, so that the lancet 1 is inhibited from moving further in the retreating direction N2, as shown in FIGS. 28B and 28C. At this point, the column-shaped portion 89Cb falls in the cutaway portions 86Ca of the first member 80C. This causes the movable portions 86C to be inwardly displaced thus to reduce the width of the gap 86CA, so that the movable portions 86C of the first member 80C apply a pressing force to the lancet 1. In addition, when the column-shaped portion 89Cb fits into the cutaway portions 86Ca, the user feels a click, to know that the lancet 1 has been properly loaded in the lancet holder 8C.

In contrast, the removal of the lancet 1 from the lancet holder 8C is performed by moving the second member 81C in the lancing direction N1. The second member 81C may be moved via the lancet discharge mechanism 5 (see FIGS. 14A and 14B) according to the first embodiment.

As seen from FIGS. 28B and 28C, moving the column-shaped portion 89Cb in the lancing direction N1 when the column-shaped portion 89Cb is fitted in the cutaway portions 86Bb causes the column-shaped portion 89b to be disengaged and to move through the main portion 86CA' of the gap 86CA. This expands the main portion 86CA' of the gap 86CA by outwardly displacing the movable portions 86C, thereby reducing the pressing force so far applied to the lancet 1 by the movable portions 86C. This ensures easy removal of the lancet 1 from the lancet holder 8. As seen from FIGS. 28A and 28B, moving the column-shaped portion 89Cb farther in the lancing direction N1 causes the lancet 1 to be discharged from the lancet holder 8C, since the movable portions 86C is barely applying a pressing force to the lancet 1. At this point, the column-shaped portion 89Cb falls in the cutaway portions 86Cb. Accordingly, the user recognizes that the lancet 1 has been discharged from the lancet holder 8C upon feeling a click when the column-shaped portion 89Cb fits into the cutaway portions 86Cb.

The foregoing structure of the cutaway portions 86Cb of the movable portion 86C may be modified in various manners, as shown in FIGS. 29A to 29F. Cutaway portions 86Db to 86Ib shown therein are shaped such that gaps 86DA to 86IA become wider at a position farther ahead in the lancing direction N1.

Figure 29:
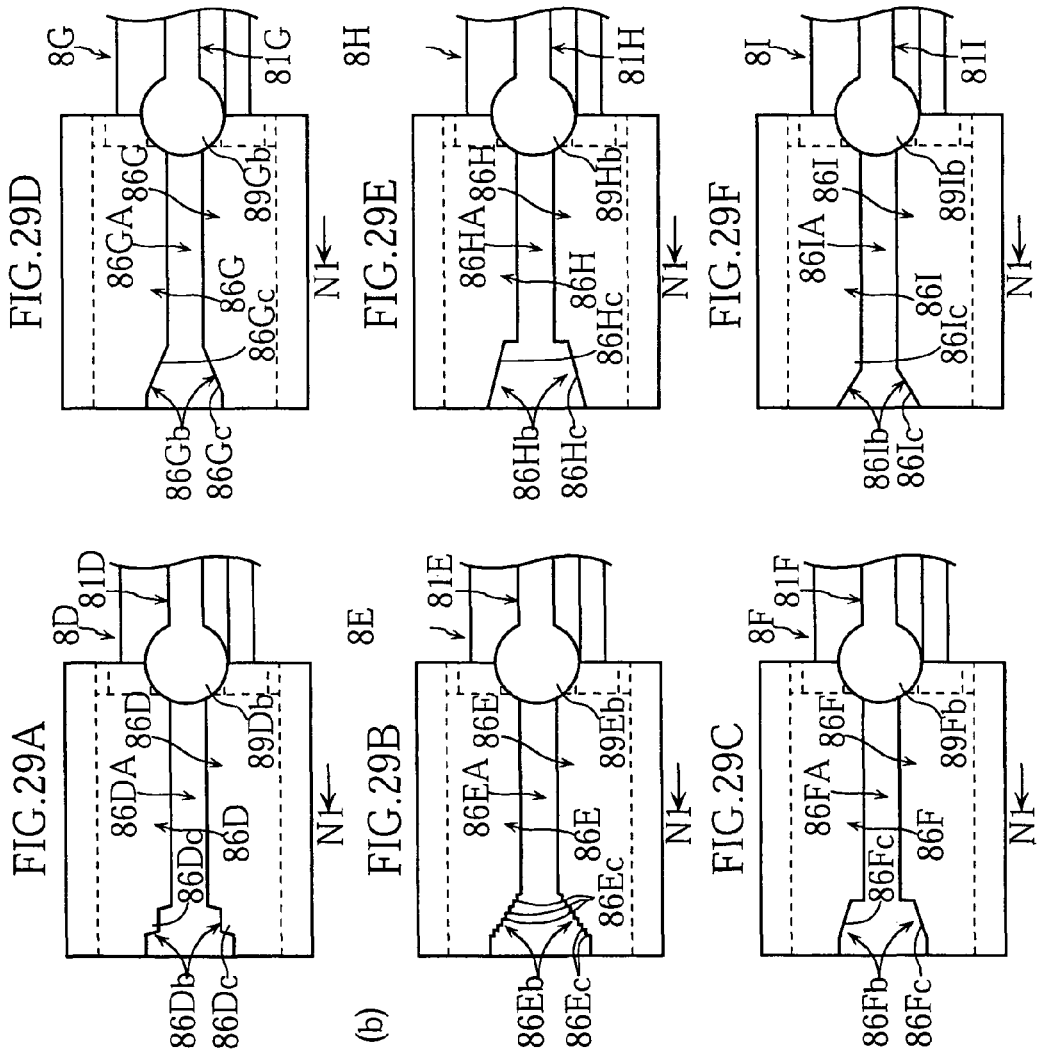
FIG. 29A to 29F are fragmentary plan views showing different lancet holders.

Specifically, the cutaway portion 86Db shown in FIG. 29A includes a stepped portion 86Dc, so that the width of the gap 86DA becomes wider sequentially at the stepped portion 86Dc. The cutaway portion 86Eb shown in FIG. 29B includes a plurality of stepped portions 86Ec in a stair shape, so that the gap 86EA becomes wider over a number of stages at the stepped portion 86Ec. The cutaway portions 86Fb to 86Ib shown in FIGS. 29C to 29F respectively include tapered portions 86Fc to 86Ic, so that the tapered portions 86Fc to 86Ic continuously expand the width of the gaps 86FA to 86IA.

In the case where the movable portions 86D to 86I include the cutaway portions 86Db to 86Ib, the movable portions 86D to 86I return to the natural state once the column-shaped portions 89Db to 89Ib fit in the cutaway portions 86Db to 86Ib, thereby applying a returning spring force to the column-shaped portion 89Db to 89Ib. When this spring force of the movable portions 86D to 86I acts on the column-shaped portions 89Db to 89Ib, the force may drive the column-shaped portion 89Db to 89Ib, and hence the second member 81D to 81I to abruptly move in the lancing direction N1, thus causing the lancet 1 (see FIG. 2) to jump out of the lancet holder 8D to 8I.

In the lancet holder 8D to 8I, however, because of the shapes of the foregoing cutaway portions 86Db to 86Ib, the width of the gap 86DA to 86IA is continuously or incrementally reduced when the column-shaped portion 89Db to 89Ib moves in the lancing direction N1. Accordingly, the movable portions 86D to 86I gradually return to the natural state, rather than abruptly. This prevents the column-shaped portion 89Db to 89Ib from being abruptly subjected to a large force. Therefore, the lancet holder 8D to 8I can prevent the lancet 1 (see FIG. 2) from jumping out, when discharging the lancet 1.

Here, in order to assure the foregoing advantage with respect to the cutaway portions 86Fb to 86Ib including the tapered portions 86Fc to 86Ic, it is preferable to form the tapered portions 86Fc to 86Ic in a gentle slope with respect to the lancing direction N1, specifically in a range of 10 to 45 degrees, for example.

Figure 30:
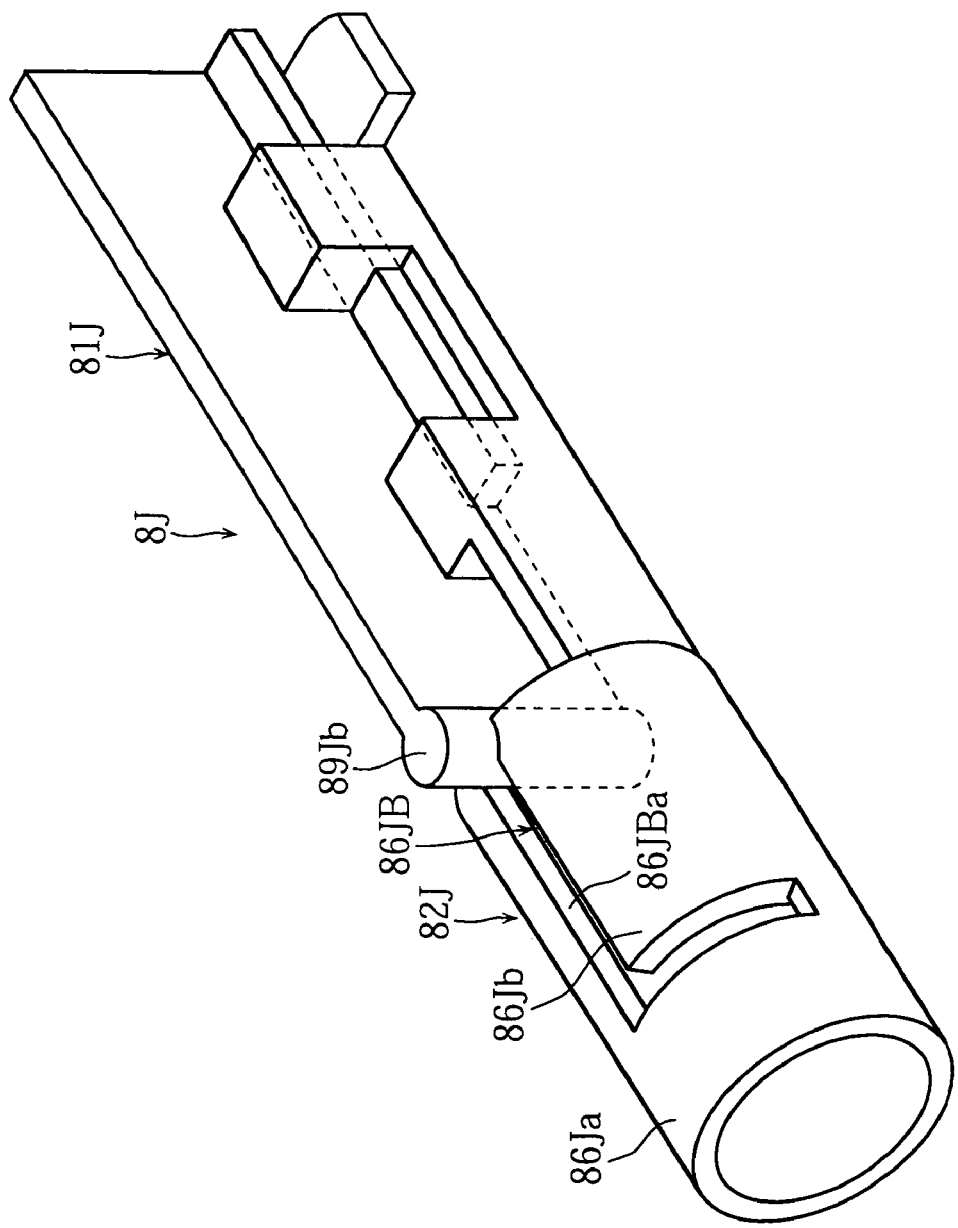
FIG. 30 is a perspective view showing another lancet holder.

The movable portions 86, 86C to 86I according to the fourth and the fifth embodiments of the present invention do not necessarily have to constitute a pair. For example as shown in FIG. 30, a lancet holder 8J may be designed such that a holder body 82J includes a fixed portion 86Ja and a movable portion 86Jb located so as to oppose the fixed portion 86Ja across a gap 86JB. With such structure, moving the column-shaped portion 89Jb of the second member 81J through a main portion 86Jba of the gap 86JB can displace the movable portion 86Jb with respect to the fixed portion 86Ja. This results in a decrease in the pressing force so far applied to the lancet 1 by the movable portion 86Jb, thus allowing easy removal of the lancet 1 from the lancet holder 8J.

Figure 31A:
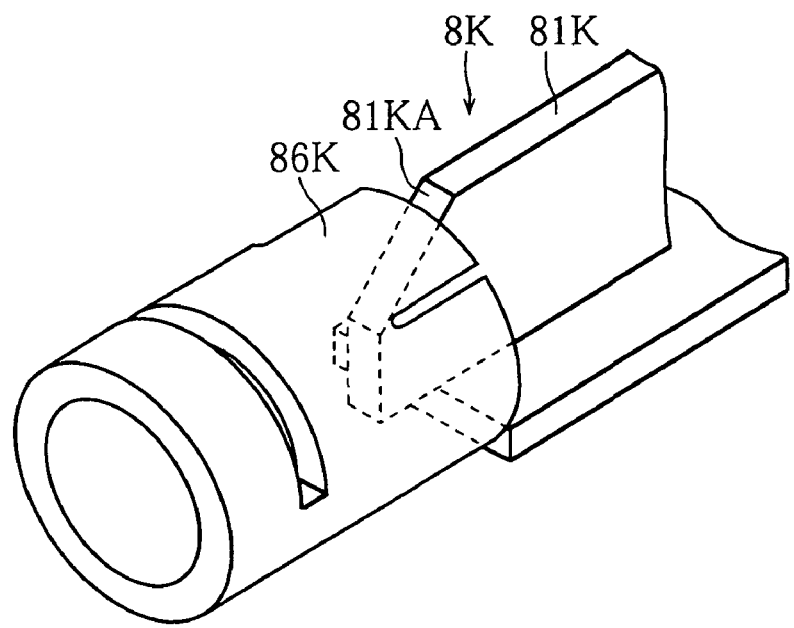
FIG. 31A is a fragmentary perspective view and FIG. 31B is a cross sectional view, respectively showing still another lancet holder.
Figure 31B:
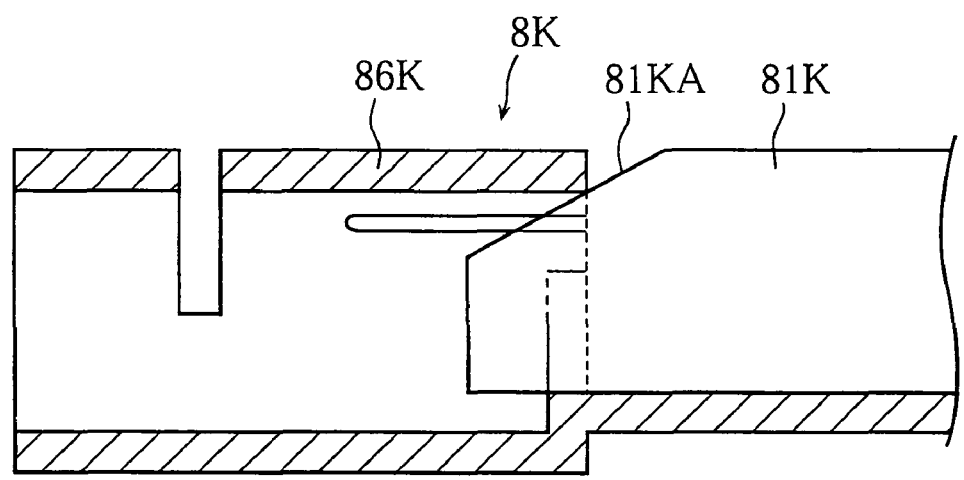
Figure 32A:
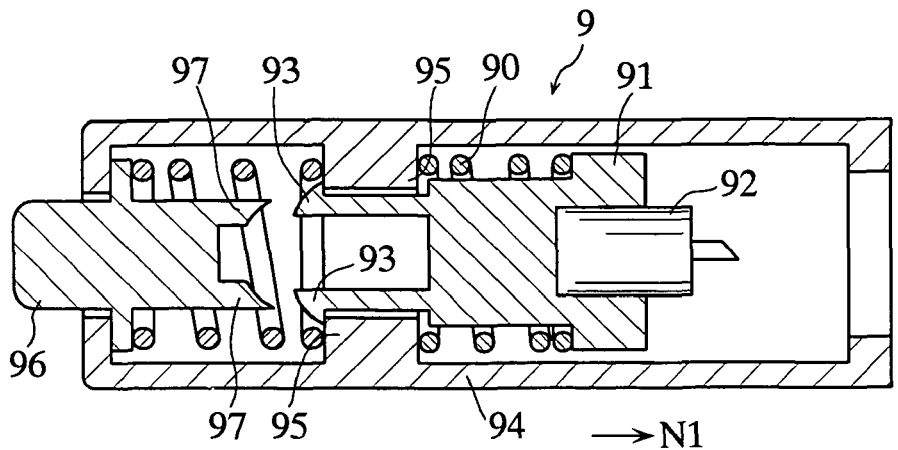
FIGS. 32A to 32C are cross-sectional views showing a conventional lancing apparatus.
Figure 32B:
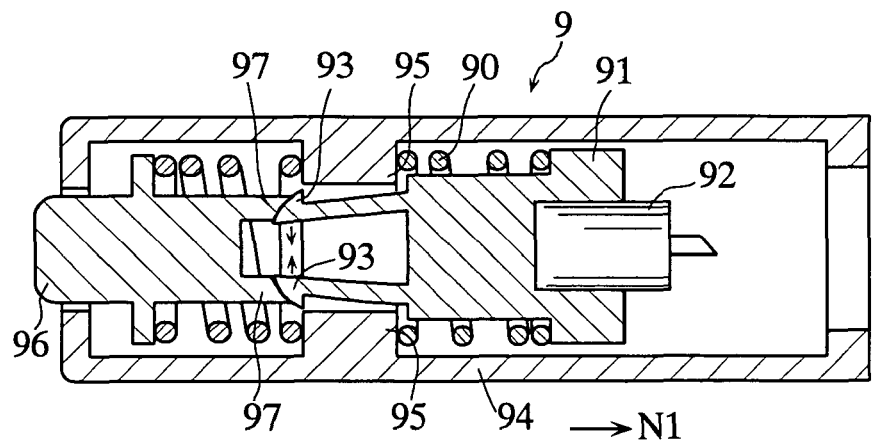
Figure 32C:
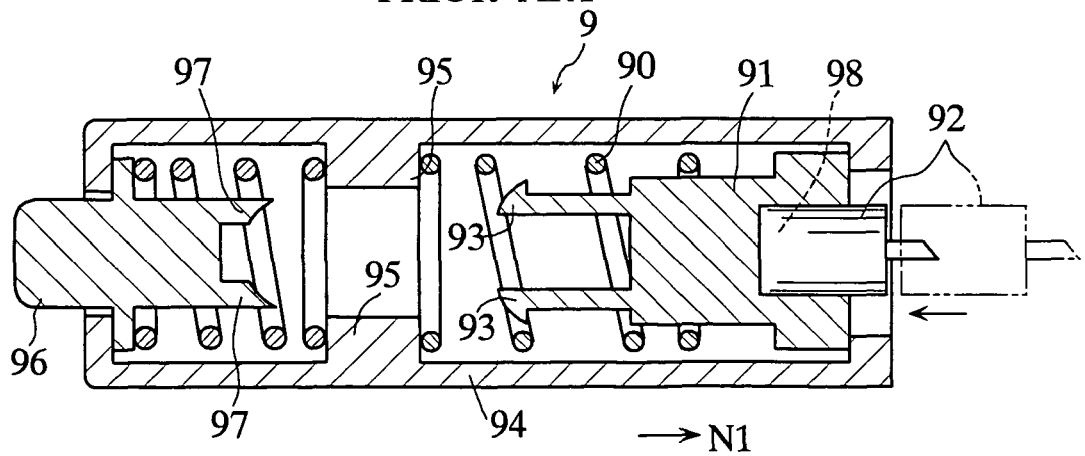

In a lancet holder 8K shown in FIGS. 31A and 31B, a second member 81K includes a tapered portion 81KA at an end portion, so as to outwardly displace a movable portion 86K. With such structure, since the movable portion 86K touches different regions of the tapered portion 81KA when the second member 81K is moved, the movable portion 86K can be thus displaced.

The present invention may be modified in various manners without limitation to the foregoing embodiments. To cite a few examples, while the lancing apparatus X is constituted such that a spring force of the coil spring Sp is applied to the moving plate 31 so as to move the lancet holder 32, an elastic material other than the coil spring Sp may be employed to apply a spring force to the moving plate 31, or the moving plate may be moved by a driving force such as a pneumatic power or an electromagnetic power. Further, the moving plate may be omitted so that the driving force is directly applied to the lancet holder, to thus move the lancet holder.

While the second member of the lancet holder is provided as an independent component from other constituents including the pushing member 50 (see FIGS. 14A and 14B) of the lancet discharge mechanism 5 in the foregoing embodiments, a constituent that serves as both the second member and the pushing member may be provided as a unified member.

The invention claimed is:

1. A lancing apparatus comprising a lancet holder for retaining a lancet and a lancet moving mechanism for moving the lancet, the lancet including a main body and a needle projecting from the body, the lancet holder being moved in a lancing direction from a standby position to a lancing position together with the lancet in response to movement of the lancet moving mechanism so as to cause the lancet to stick into an object, the lancet being inserted into the lancet holder in a retreating direction opposite to the lancing direction, thus to be retained by the lancet holder, wherein the lancet holder includes a first member and a second member that are movable relative to each other, the second member being in direct contact with the first member and being movable relative to the first member between a fixing position in which the main body of the lancet is fixed to the lancet holder with a first fixing force for limiting axial removal of the lancet from the lancet holder and a non-fixing position in which the main body of the lancet is held by the lancet holder with a second fixing force smaller than the first fixing force for facilitated axial removal of the lancet from the lancet holder, the second member being moved in the lancing direction together with the first member and the lancet in response to the movement of the lancet moving mechanism for causing the lancet to stick into the object when the second member is held in the fixing position for fixing the lancet to the lancet holder.

2. The lancing apparatus according to claim 1, wherein at least either of the first and the second members applies a pressing force to the lancet for fixing the lancet.

3. The lancing apparatus according to claim 2, wherein, when loading the lancet, the lancet moves relative to the first member, while the second member moves together with the lancet relative to the first member in the retreating direction from the non-fixing position toward the fixing position, and wherein the lancet holder applies a greater pressing force to the lancet when the second member is located at the fixing position than when the second member is at the non-fixing position.

4. The lancing apparatus according to claim 3, further comprising fixing means that applies a pressing force to the lancet for fixing the lancet when the second member is at the fixing position.

5. The lancing apparatus according to claim 4, wherein the first and the second members respectively include a first engaging portion and a second engaging portion that are engaged with each other when the second member is at the fixing position, the fixing means comprising the first and second engaging portions.

6. The lancing apparatus according to claim 5, wherein at least one of the first and the second engaging portions projects toward the other of the first and the second engaging portions.

7. The lancing apparatus according to claim 5, wherein one of the first and the second engaging portions comprises a recess, and the other of the first and the second engaging portions comprises a projection to be fitted into the recess.

8. The lancing apparatus according to claim 3, wherein the first member includes a pressing portion that applies a pressing force to the lancet, and wherein the second member includes a working portion that displaces at least a part of the pressing portion from the lancet when the second member is located at the non-fixing position or between the non-fixing position and the fixing position.

9. The lancing apparatus according to claim 8, wherein the pressing portion includes a pair of movable portions, wherein a gap is provided between the pair of movable portions for allowing the working portion to move, and wherein the gap is expanded when the working portion moves through the gap, so that at least a part of the movable portions is displaced so as to separate from the lancet.

10. The lancing apparatus according to claim 9, wherein at least one of the movable portions includes at least one cutaway that defines a part of the gap, and that the working portion fits into.

11. The lancing apparatus according to claim 10, wherein said at least one cutaway comprises a first cutaway portion into which the working portion is fitted in fixing the lancet, and a second cutaway portion into which the working portion is fitted in discharging the lancet.

12. The lancing apparatus according to claim 10, wherein said at least one cutaway comprises a cutaway portion arranged to make the gap continuously or incrementally narrower when the working portion relatively moves with respect to the first member in the lancing direction.

13. The lancing apparatus according to claim 12, wherein the cutaway portion includes a tapered portion that makes the gap wider continuously as proceeding in the lancing direction.

14. The lancing apparatus according to claim 12, wherein the cutaway portion includes at least one stepped portion that makes the gap wider sequentially as proceeding in the lancing direction.

15. The lancing apparatus according to claim 12, wherein the cutaway portion includes a tapered portion that makes the gap wider continuously as proceeding in the lancing direction, and also includes at least one stepped portion that makes the gap wider sequentially as proceeding in the lancing direction.

16. The lancing apparatus according to claim 8, wherein the pressing portion includes a fixed portion and a movable portion,
wherein a gap is provided between the fixed portion and the movable portion for allowing the working portion to move, and
wherein the gap is expanded when the working portion moves through the gap, so that at least a part of the movable portion is displaced so as to separate from the lancet.

17. The lancing apparatus according to claim 1, wherein the second member includes a pair of movable portions for holding the lancet therebetween, and
wherein the movable portions are displaced away from the lancet when the second member is relatively moved with respect to the first member in the lancing direction, but displaced toward the lancet when the second member is relatively moved with respect to the first member in the retreating direction.

18. The lancing apparatus according to claim 17, wherein the lancet comprises a recess, and
wherein the movable portion comprises an engaging portion to be engaged with the recess.

19. The lancing apparatus according to claim 1, further comprising a pushing member that moves the second member in the lancing direction.

20. The lancing apparatus according to claim 19, wherein the pushing member includes a working portion that interferes with the second member and an operating portion to be manipulated so as to move the working portion.

21. A lancing apparatus comprising a lancet holder for retaining a lancet and a lancet moving mechanism for moving the lancet, the lancet including a main body and a needle projecting from the body, the lancet holder being moved in a lancing direction from a standby position to a lancing position together with the lancet in response to movement of the lancet moving mechanism so as to cause the lancet to stick into an object, the lancet being inserted into the lancet holder in a retreating direction opposite to the lancing direction, thus to be retained by the lancet holder,
wherein the lancet holder includes a first member and a second member that are movable relative to each other in a needle extending direction, the first member being connected to the lancet moving mechanism for movement therewith in the lancing direction, the second member being in direct contact with the first member and being movable relative to the first member between a fixing position in which the main body of the lancet is fixed to the lancet holder and a non-fixing position in which the main body of the lancet is allowed to be removed from the lancet holder, the second member including a movable fixing portion that moves in a direction crossing the needle extending direction for fixing contact with the main body of the lancet in response to the movement of the second member from the non-fixing position to the fixing position, the first member being moved in the lancing direction together with the second member and the lancet for causing the lancet to stick into the object when the second member is held in the fixing position for fixing the lancet to the lancet holder.

* * * * *